(12) United States Patent
Lee et al.

(10) Patent No.: US 11,110,283 B2
(45) Date of Patent: Sep. 7, 2021

(54) NEUROSTIMULATION LEADS FOR TRIAL NERVE STIMULATION AND METHODS OF USE

(71) Applicant: Axonics, Inc., Irvine, CA (US)

(72) Inventors: Henry Lee, Irvine, CA (US); David Marvicsin, Irvine, CA (US); Trishna Dave, Irvine, CA (US)

(73) Assignee: AXONICS, INC., Irvine, CA (US)

( * ) Notice: Subject to any disclaimer, the term of this patent is extended or adjusted under 35 U.S.C. 154(b) by 0 days.

(21) Appl. No.: 16/281,857

(22) Filed: Feb. 21, 2019

(65) Prior Publication Data

US 2019/0255339 A1   Aug. 22, 2019

Related U.S. Application Data

(60) Provisional application No. 62/633,806, filed on Feb. 22, 2018.

(51) Int. Cl.
*A61N 1/05* (2006.01)
*A61N 1/36* (2006.01)
(Continued)

(52) U.S. Cl.
CPC ....... *A61N 1/37518* (2017.08); *A61N 1/0558* (2013.01); *A61N 1/36062* (2017.08);
(Continued)

(58) Field of Classification Search
CPC .............. A61N 1/37518; A61N 1/0558; A61N 1/37205; A61N 1/36062; A61N 1/36107;
(Continued)

(56) References Cited

U.S. PATENT DOCUMENTS 3,057,356 A   10/1962   Greatbatch
3,348,548 A   10/1967   Chardack
(Continued)

FOREIGN PATENT DOCUMENTS

AT   520440   9/2011
AU   4664800   11/2000
(Continued)

OTHER PUBLICATIONS

US 9,601,939 B2, 03/2017, Cong et al. (withdrawn)
(Continued)

*Primary Examiner* — Carl H Layno
*Assistant Examiner* — Anh-Khoa N Dinh
(74) *Attorney, Agent, or Firm* — Kilpatrickt Townsend & Stockton LLP

(57) ABSTRACT

Devices and methods for providing neurostimulation to a patient, particularly in trial systems assessing suitability of a permanently implanted neurostimulation, are provided herein. In one aspect, a trial neurostimulation lead includes a coiled conductor coupled to a proximal contact connector having a retention flange that withstands tensile force from tension in the lead so as to maintain the electrical connection during a trial period. In another aspect, a trial neurostimulation system includes a lead extension that includes a regression stopper between the implanted distal connector and proximal lead disposed outside the body to prevent regression of the lead through a secondary incision, thereby preventing infection and facilitating explant of the system. Methods of assembling and utilizing such leads and systems are detailed herein.

37 Claims, 18 Drawing Sheets

(51) Int. Cl.
*A61N 1/372* (2006.01)
*A61N 1/375* (2006.01)

(52) U.S. Cl.
CPC ...... *A61N 1/37205* (2013.01); *A61N 1/36071* (2013.01); *A61N 1/36107* (2013.01)

(58) Field of Classification Search
CPC ............ A61N 1/36071; A61N 1/37241; A61N 1/36017; A61N 1/0551; A61N 1/372
See application file for complete search history.

(56) References Cited

U.S. PATENT DOCUMENTS

| | | |
|---|---|---|
| 3,646,940 A | 3/1972 | Timm et al. |
| 3,824,129 A | 7/1974 | Fagan, Jr. |
| 3,825,015 A | 7/1974 | Berkovits |
| 3,888,260 A | 6/1975 | Fischell |
| 3,902,501 A | 9/1975 | Citron et al. |
| 3,939,843 A | 2/1976 | Smyth |
| 3,942,535 A | 3/1976 | Schulman |
| 3,970,912 A | 7/1976 | Hoffman |
| 3,995,623 A | 12/1976 | Blake et al. |
| 4,019,518 A | 4/1977 | Maurer et al. |
| 4,044,774 A | 8/1977 | Corbin et al. |
| 4,082,097 A | 4/1978 | Mann et al. |
| 4,135,518 A * | 1/1979 | Dutcher ................ A61N 1/057 600/374 |
| 4,141,365 A | 2/1979 | Fischell et al. |
| 4,166,469 A | 9/1979 | Littleford |
| 4,236,529 A | 12/1980 | Little |
| 4,269,198 A | 5/1981 | Stokes |
| 4,285,347 A | 8/1981 | Hess |
| 4,340,062 A | 7/1982 | Thompson et al. |
| 4,379,462 A | 4/1983 | Borkan et al. |
| 4,407,303 A | 10/1983 | Akerstrom |
| 4,437,475 A | 3/1984 | White |
| 4,512,351 A | 4/1985 | Pohndorf |
| 4,550,731 A | 11/1985 | Batina et al. |
| 4,558,702 A | 12/1985 | Barreras et al. |
| 4,654,880 A | 3/1987 | Sontag |
| 4,662,382 A | 5/1987 | Sluetz et al. |
| 4,719,919 A | 1/1988 | Marchosky et al. |
| 4,721,118 A | 1/1988 | Harris |
| 4,722,353 A | 2/1988 | Sluetz |
| 4,744,371 A | 5/1988 | Harris |
| 4,800,898 A | 1/1989 | Hess et al. |
| 4,848,352 A | 7/1989 | Pohndorf et al. |
| 4,860,446 A | 8/1989 | Lessar et al. |
| 4,957,118 A | 9/1990 | Erlebacher |
| 4,989,617 A | 2/1991 | Memberg et al. |
| 5,012,176 A | 4/1991 | Laforge |
| 5,052,407 A | 10/1991 | Hauser et al. |
| 5,197,466 A | 3/1993 | Marchosky et al. |
| 5,204,611 A | 4/1993 | Nor et al. |
| 5,255,691 A | 10/1993 | Otten |
| 5,257,634 A | 11/1993 | Kroll |
| 5,342,408 A | 8/1994 | Decoriolis et al. |
| 5,366,493 A | 11/1994 | Scheiner et al. |
| 5,439,485 A | 8/1995 | Mar et al. |
| 5,476,499 A | 12/1995 | Hirschberg |
| 5,484,445 A | 1/1996 | Knuth |
| 5,545,206 A | 4/1996 | Carson |
| 5,571,148 A | 11/1996 | Loeb et al. |
| 5,592,070 A | 1/1997 | Mino |
| 5,637,981 A | 6/1997 | Nagai et al. |
| 5,676,162 A | 10/1997 | Larson, Jr. et al. |
| 5,683,447 A | 11/1997 | Bush et al. |
| 5,690,693 A | 11/1997 | Wang et al. |
| 5,702,428 A | 12/1997 | Tippey et al. |
| 5,702,431 A | 12/1997 | Wang et al. |
| 5,712,795 A | 1/1998 | Layman et al. |
| 5,713,939 A | 2/1998 | Nedungadi et al. |
| 5,733,313 A | 3/1998 | Barreras, Sr. et al. |
| 5,735,887 A | 4/1998 | Barreras, Sr. et al. |
| 5,741,316 A | 4/1998 | Chen et al. |
| 5,871,532 A | 2/1999 | Schroeppel |
| 5,876,423 A | 3/1999 | Braun |
| 5,902,331 A | 5/1999 | Bonner et al. |
| 5,948,006 A | 9/1999 | Mann |
| 5,949,632 A | 9/1999 | Barreras, Sr. et al. |
| 5,957,965 A | 9/1999 | Moumane et al. |
| 5,991,665 A | 11/1999 | Wang et al. |
| 6,027,456 A | 2/2000 | Feler et al. |
| 6,035,237 A | 3/2000 | Schulman et al. |
| 6,052,624 A | 4/2000 | Mann |
| 6,055,456 A | 4/2000 | Gerber |
| 6,057,513 A | 5/2000 | Ushikoshi et al. |
| 6,067,474 A | 5/2000 | Schulman et al. |
| 6,075,339 A | 6/2000 | Reipur et al. |
| 6,076,017 A | 6/2000 | Taylor et al. |
| 6,081,097 A | 6/2000 | Seri et al. |
| 6,083,247 A | 7/2000 | Rutten et al. |
| 6,104,957 A | 8/2000 | Alo et al. |
| 6,104,960 A | 8/2000 | Duysens et al. |
| 6,138,681 A | 10/2000 | Chen et al. |
| 6,165,180 A | 12/2000 | Cigaina et al. |
| 6,166,518 A | 12/2000 | Echarri et al. |
| 6,169,387 B1 | 1/2001 | Kaib |
| 6,172,556 B1 | 1/2001 | Prentice |
| 6,178,353 B1 | 1/2001 | Griffith et al. |
| 6,181,105 B1 | 1/2001 | Cutolo et al. |
| 6,191,365 B1 | 2/2001 | Avellanet |
| 6,208,894 B1 | 3/2001 | Schulman et al. |
| 6,212,430 B1 | 4/2001 | Kung |
| 6,212,431 B1 | 4/2001 | Hahn et al. |
| 6,221,513 B1 | 4/2001 | Lasater |
| 6,227,204 B1 | 5/2001 | Baumann et al. |
| 6,240,322 B1 | 5/2001 | Peterfeso et al. |
| 6,243,608 B1 | 6/2001 | Pauly et al. |
| 6,246,911 B1 | 6/2001 | Seligman |
| 6,249,703 B1 | 6/2001 | Stanton et al. |
| 6,265,789 B1 | 7/2001 | Honda et al. |
| 6,275,737 B1 | 8/2001 | Mann |
| 6,278,258 B1 | 8/2001 | Echarri et al. |
| 6,305,381 B1 | 10/2001 | Weijand et al. |
| 6,306,100 B1 | 10/2001 | Prass |
| 6,315,721 B2 | 11/2001 | Schulman et al. |
| 6,316,909 B1 | 11/2001 | Honda et al. |
| 6,321,118 B1 | 11/2001 | Hahn |
| 6,327,504 B1 | 12/2001 | Dolgin et al. |
| 6,354,991 B1 | 3/2002 | Gross et al. |
| 6,360,750 B1 | 3/2002 | Gerber et al. |
| 6,381,496 B1 | 4/2002 | Meadows et al. |
| 6,393,325 B1 | 5/2002 | Mann et al. |
| 6,438,423 B1 | 8/2002 | Rezai et al. |
| 6,442,434 B1 | 8/2002 | Zarinetchi et al. |
| 6,453,198 B1 | 9/2002 | Torgerson et al. |
| 6,466,817 B1 | 10/2002 | Kaula et al. |
| 6,473,652 B1 | 10/2002 | Sarwal et al. |
| 6,500,141 B1 | 12/2002 | Irion |
| 6,505,075 B1 | 1/2003 | Weiner |
| 6,505,077 B1 | 1/2003 | Kast et al. |
| 6,510,347 B2 | 1/2003 | Borkan |
| 6,516,227 B1 | 2/2003 | Meadows et al. |
| 6,517,227 B2 | 2/2003 | Stidham et al. |
| 6,542,846 B1 | 4/2003 | Miller et al. |
| 6,553,263 B1 | 4/2003 | Meadows et al. |
| 6,584,355 B2 | 6/2003 | Stessman |
| 6,600,954 B2 | 7/2003 | Cohen et al. |
| 6,609,031 B1 | 8/2003 | Law et al. |
| 6,609,032 B1 | 8/2003 | Woods et al. |
| 6,609,945 B2 | 8/2003 | Jimenez et al. |
| 6,652,449 B1 | 11/2003 | Gross et al. |
| 6,662,051 B1 | 12/2003 | Eraker et al. |
| 6,664,763 B2 | 12/2003 | Echarri et al. |
| 6,685,638 B1 | 2/2004 | Taylor et al. |
| 6,721,603 B2 | 4/2004 | Zabara et al. |
| 6,735,474 B1 | 5/2004 | Loeb et al. |
| 6,745,077 B1 | 6/2004 | Griffith et al. |
| 6,792,314 B2 | 9/2004 | Byers et al. |
| 6,809,701 B2 | 10/2004 | Amundson et al. |
| 6,836,684 B1 | 12/2004 | Rijkhoff et al. |
| 6,847,849 B2 | 1/2005 | Mamo et al. |
| 6,892,098 B2 | 5/2005 | Ayal et al. |

(56) References Cited

U.S. PATENT DOCUMENTS

| | | |
|---|---|---|
| 6,895,280 B2 | 5/2005 | Meadows et al. |
| 6,896,651 B2 | 5/2005 | Gross et al. |
| 6,901,287 B2 | 5/2005 | Davis et al. |
| 6,941,171 B2 | 9/2005 | Mann et al. |
| 6,971,393 B1 | 12/2005 | Mamo et al. |
| 6,989,200 B2 | 1/2006 | Byers et al. |
| 6,990,376 B2 | 1/2006 | Tanagho et al. |
| 6,999,819 B2 | 2/2006 | Swoyer et al. |
| 7,051,419 B2 | 5/2006 | Schrom et al. |
| 7,054,689 B1 | 5/2006 | Whitehurst et al. |
| 7,069,081 B2 | 6/2006 | Biggs et al. |
| 7,092,764 B2 | 8/2006 | Williams et al. |
| 7,127,298 B1 | 10/2006 | He et al. |
| 7,131,996 B2 | 11/2006 | Wasserman et al. |
| 7,142,925 B1 | 11/2006 | Bhadra et al. |
| 7,146,219 B2 | 12/2006 | Sieracki et al. |
| 7,151,914 B2 | 12/2006 | Brewer |
| 7,167,749 B2 | 1/2007 | Biggs et al. |
| 7,167,756 B1 | 1/2007 | Torgerson et al. |
| 7,177,690 B2 | 2/2007 | Woods et al. |
| 7,177,698 B2 | 2/2007 | Klosterman et al. |
| 7,181,286 B2 | 2/2007 | Sieracki et al. |
| 7,184,836 B1 | 2/2007 | Meadows et al. |
| 7,187,978 B2 | 3/2007 | Malek et al. |
| 7,191,005 B2 | 3/2007 | Stessman |
| 7,212,110 B1 | 5/2007 | Martin et al. |
| 7,225,028 B2 | 5/2007 | Della Santina et al. |
| 7,225,032 B2 | 5/2007 | Schmeling et al. |
| 7,231,254 B2 | 6/2007 | DiLorenzo |
| 7,234,853 B2 | 6/2007 | Givoletti |
| 7,239,918 B2 | 7/2007 | Strother et al. |
| 7,245,972 B2 | 7/2007 | Davis |
| 7,286,880 B2 | 10/2007 | Olson et al. |
| 7,295,878 B1 | 11/2007 | Meadows et al. |
| 7,305,268 B2 | 12/2007 | Gliner et al. |
| 7,317,948 B1 | 1/2008 | King et al. |
| 7,324,852 B2 | 1/2008 | Barolat et al. |
| 7,324,853 B2 | 1/2008 | Ayal et al. |
| 7,328,068 B2 | 2/2008 | Spinelli et al. |
| 7,330,764 B2 | 2/2008 | Swoyer et al. |
| 7,359,751 B1 | 4/2008 | Erickson et al. |
| 7,369,894 B2 | 5/2008 | Gerber |
| 7,386,348 B2 | 6/2008 | North et al. |
| 7,387,603 B2 | 6/2008 | Gross et al. |
| 7,396,265 B2 | 7/2008 | Darley et al. |
| 7,415,308 B2 | 8/2008 | Gerber et al. |
| 7,444,181 B2 | 10/2008 | Shi et al. |
| 7,444,184 B2 | 10/2008 | Boveja et al. |
| 7,450,991 B2 | 11/2008 | Smith et al. |
| 7,460,911 B2 | 12/2008 | Cosendai et al. |
| 7,463,928 B2 | 12/2008 | Lee et al. |
| 7,470,236 B1 | 12/2008 | Kelleher et al. |
| 7,483,752 B2 | 1/2009 | Von Arx et al. |
| 7,486,048 B2 | 2/2009 | Tsukamoto et al. |
| 7,496,404 B2 | 2/2009 | Meadows et al. |
| 7,515,967 B2 | 4/2009 | Phillips et al. |
| 7,532,936 B2 | 5/2009 | Erickson et al. |
| 7,539,538 B2 | 5/2009 | Parramon et al. |
| 7,551,960 B2 | 6/2009 | Forsberg et al. |
| 7,555,346 B1 | 6/2009 | Woods et al. |
| 7,565,203 B2 | 7/2009 | Greenberg et al. |
| 7,578,819 B2 | 8/2009 | Bleich et al. |
| 7,580,752 B2 | 8/2009 | Gerber et al. |
| 7,582,053 B2 | 9/2009 | Gross et al. |
| 7,590,451 B2 | 9/2009 | Tronnes et al. |
| 7,617,002 B2 | 11/2009 | Goetz |
| 7,640,059 B2 | 12/2009 | Forsberg et al. |
| 7,643,880 B2 | 1/2010 | Tanagho et al. |
| 7,650,192 B2 | 1/2010 | Wahlstrand |
| 7,676,275 B1 | 3/2010 | Farazi et al. |
| 7,706,889 B2 | 4/2010 | Gerber et al. |
| 7,720,547 B2 | 5/2010 | Denker et al. |
| 7,725,191 B2 | 5/2010 | Greenberg et al. |
| 7,734,355 B2 | 6/2010 | Cohen et al. |
| 7,738,963 B2 | 6/2010 | Hickman et al. |
| 7,738,965 B2 | 6/2010 | Phillips et al. |
| 7,747,330 B2 | 6/2010 | Nolan et al. |
| 7,771,838 B1 | 8/2010 | He et al. |
| 7,774,069 B2 | 8/2010 | Olson et al. |
| 7,801,619 B2 | 9/2010 | Gerber et al. |
| 7,813,803 B2 | 10/2010 | Heruth et al. |
| 7,813,809 B2 | 10/2010 | Strother et al. |
| 7,826,901 B2 | 11/2010 | Lee et al. |
| 7,848,818 B2 | 12/2010 | Barolat et al. |
| 7,878,207 B2 | 2/2011 | Goetz et al. |
| 7,881,783 B2 | 2/2011 | Bonde et al. |
| 7,894,913 B2 | 2/2011 | Boggs et al. |
| 7,904,167 B2 | 3/2011 | Klosterman et al. |
| 7,912,555 B2 | 3/2011 | Swoyer et al. |
| 7,925,357 B2 | 4/2011 | Phillips et al. |
| 7,932,696 B2 | 4/2011 | Peterson |
| 7,933,656 B2 | 4/2011 | Sieracki et al. |
| 7,935,051 B2 | 5/2011 | Miles et al. |
| 7,937,158 B2 | 5/2011 | Erickson et al. |
| 7,952,349 B2 | 5/2011 | Huang et al. |
| 7,957,818 B2 | 6/2011 | Swoyer |
| 7,979,119 B2 | 7/2011 | Kothandaraman et al. |
| 7,979,126 B2 | 7/2011 | Payne et al. |
| 7,988,507 B2 | 8/2011 | Darley et al. |
| 8,000,782 B2 | 8/2011 | Gharib et al. |
| 8,000,800 B2 | 8/2011 | Takeda et al. |
| 8,000,805 B2 | 8/2011 | Swoyer et al. |
| 8,005,535 B2 | 8/2011 | Gharib et al. |
| 8,005,549 B2 | 8/2011 | Boser et al. |
| 8,005,550 B2 | 8/2011 | Boser et al. |
| 8,019,423 B2 | 9/2011 | Possover |
| 8,019,443 B2 | 9/2011 | Schleicher et al. |
| 8,024,047 B2 | 9/2011 | Olson et al. |
| 8,036,756 B2 | 10/2011 | Swoyer et al. |
| 8,044,635 B2 | 10/2011 | Peterson |
| 8,050,769 B2 | 11/2011 | Gharib et al. |
| 8,055,337 B2 | 11/2011 | Moffitt et al. |
| 8,068,912 B2 | 11/2011 | Kaula et al. |
| 8,083,663 B2 | 12/2011 | Gross et al. |
| 8,103,360 B2 | 1/2012 | Foster |
| 8,116,862 B2 | 2/2012 | Stevenson et al. |
| 8,121,701 B2 | 2/2012 | Woods et al. |
| 8,129,942 B2 | 3/2012 | Park et al. |
| 8,131,358 B2 | 3/2012 | Moffitt et al. |
| 8,140,168 B2 | 3/2012 | Olson et al. |
| 8,145,324 B1 | 3/2012 | Stevenson et al. |
| 8,150,530 B2 | 4/2012 | Wesselink |
| 8,175,717 B2 | 5/2012 | Haller et al. |
| 8,180,451 B2 | 5/2012 | Hickman et al. |
| 8,180,452 B2 | 5/2012 | Shaquer |
| 8,180,461 B2 | 5/2012 | Mamo et al. |
| 8,214,042 B2 | 7/2012 | Ozawa et al. |
| 8,214,048 B1 | 7/2012 | Whitehurst et al. |
| 8,214,051 B2 | 7/2012 | Sieracki et al. |
| 8,219,196 B2 | 7/2012 | Torgerson |
| 8,219,202 B2 | 7/2012 | Giftakis et al. |
| 8,224,460 B2 | 7/2012 | Schleicher et al. |
| 8,233,990 B2 | 7/2012 | Goetz |
| 8,255,057 B2 | 8/2012 | Fang et al. |
| 8,311,636 B2 | 11/2012 | Gerber et al. |
| 8,314,594 B2 | 11/2012 | Scott et al. |
| 8,332,040 B1 | 12/2012 | Winstrom |
| 8,340,786 B2 | 12/2012 | Gross et al. |
| 8,362,742 B2 | 1/2013 | Kallmyer |
| 8,364,281 B2 | 1/2013 | Duncan et al. |
| 8,369,943 B2 | 2/2013 | Shuros et al. |
| 8,386,048 B2 | 2/2013 | McClure et al. |
| 8,417,346 B2 | 4/2013 | Giftakis et al. |
| 8,423,146 B2 | 4/2013 | Giftakis et al. |
| 8,447,402 B1 | 5/2013 | Jiang et al. |
| 8,447,408 B2 | 5/2013 | North et al. |
| 8,457,756 B2 | 6/2013 | Rahman |
| 8,457,758 B2 | 6/2013 | Olson et al. |
| 8,467,875 B2 | 6/2013 | Bennett et al. |
| 8,480,437 B2 | 7/2013 | Dilmaghanian et al. |
| 8,494,625 B2 | 7/2013 | Hargrove |
| 8,515,545 B2 | 8/2013 | Trier |
| 8,538,530 B1 | 9/2013 | Orinski |
| 8,543,223 B2 | 9/2013 | Sage et al. |

(56) References Cited

U.S. PATENT DOCUMENTS

| | | |
|---|---|---|
| 8,544,322 B2 | 10/2013 | Minami et al. |
| 8,549,015 B2 | 10/2013 | Barolat |
| 8,554,322 B2 | 10/2013 | Olson et al. |
| 8,555,894 B2 | 10/2013 | Schulman et al. |
| 8,562,539 B2 | 10/2013 | Marino |
| 8,571,677 B2 | 10/2013 | Torgerson et al. |
| 8,577,474 B2 | 11/2013 | Rahman et al. |
| 8,588,917 B2 | 11/2013 | Whitehurst et al. |
| 8,626,314 B2 | 1/2014 | Swoyer et al. |
| 8,644,933 B2 | 2/2014 | Ozawa et al. |
| 8,655,451 B2 | 2/2014 | Klosterman et al. |
| 8,700,175 B2 | 4/2014 | Fell |
| 8,706,229 B2 | 4/2014 | Lahti et al. |
| 8,706,254 B2 | 4/2014 | Vamos et al. |
| 8,725,262 B2 | 5/2014 | Olson et al. |
| 8,725,269 B2 | 5/2014 | Nolan et al. |
| 8,738,141 B2 | 5/2014 | Smith et al. |
| 8,738,148 B2 | 5/2014 | Olson et al. |
| 8,750,985 B2 | 6/2014 | Parramon et al. |
| 8,761,897 B2 | 6/2014 | Kaula et al. |
| 8,768,452 B2 | 7/2014 | Gerber |
| 8,774,912 B2 | 7/2014 | Gerber |
| 8,855,767 B2 | 10/2014 | Faltys et al. |
| 8,918,174 B2 | 12/2014 | Woods et al. |
| 8,954,148 B2 | 2/2015 | Labbe et al. |
| 8,989,861 B2 | 3/2015 | Su et al. |
| 9,002,476 B2 | 4/2015 | Geroy et al. |
| 9,044,592 B2 | 6/2015 | Imran et al. |
| 9,050,473 B2 | 6/2015 | Woods et al. |
| 9,089,712 B2 | 7/2015 | Joshi et al. |
| 9,108,063 B2 | 8/2015 | Olson et al. |
| 9,144,680 B2 | 9/2015 | Kaula et al. |
| 9,149,635 B2 | 10/2015 | Denison et al. |
| 9,155,885 B2 | 10/2015 | Wei et al. |
| 9,166,321 B2 | 10/2015 | Smith et al. |
| 9,168,374 B2 | 10/2015 | Su |
| 9,192,763 B2 | 11/2015 | Gerber et al. |
| 9,197,173 B2 | 11/2015 | Denison et al. |
| 9,199,075 B1 | 12/2015 | Westlund |
| 9,205,255 B2 | 12/2015 | Strother et al. |
| 9,209,634 B2 | 12/2015 | Cottrill et al. |
| 9,216,294 B2 | 12/2015 | Bennett et al. |
| 9,227,055 B2 | 1/2016 | Wahlstrand et al. |
| 9,227,076 B2 | 1/2016 | Sharma et al. |
| 9,238,135 B2 | 1/2016 | Goetz et al. |
| 9,240,630 B2 | 1/2016 | Joshi |
| 9,242,090 B2 | 1/2016 | Atalar et al. |
| 9,244,898 B2 | 1/2016 | Vamos et al. |
| 9,248,292 B2 | 2/2016 | Trier et al. |
| 9,259,578 B2 | 2/2016 | Torgerson et al. |
| 9,259,582 B2 | 2/2016 | Joshi et al. |
| 9,265,958 B2 | 2/2016 | Joshi et al. |
| 9,270,134 B2 | 2/2016 | Gaddam et al. |
| 9,272,140 B2 | 3/2016 | Gerber et al. |
| 9,283,394 B2 | 3/2016 | Whitehurst et al. |
| 9,295,851 B2 | 3/2016 | Gordon et al. |
| 9,308,022 B2 | 4/2016 | Chitre et al. |
| 9,308,382 B2 | 4/2016 | Strother et al. |
| 9,314,616 B2 | 4/2016 | Wells et al. |
| 9,320,899 B2 | 4/2016 | Parramon et al. |
| 9,333,339 B2 | 5/2016 | Weiner |
| 9,352,148 B2 | 5/2016 | Stevenson et al. |
| 9,352,150 B2 | 5/2016 | Stevenson et al. |
| 9,358,039 B2 | 6/2016 | Kimmel et al. |
| 9,364,658 B2 | 6/2016 | Wechter |
| 9,375,574 B2 | 6/2016 | Kaula et al. |
| 9,393,423 B2 | 7/2016 | Parramon et al. |
| 9,399,137 B2 | 7/2016 | Parker et al. |
| 9,409,020 B2 | 8/2016 | Parker |
| 9,415,211 B2 | 8/2016 | Bradley et al. |
| 9,427,571 B2 | 8/2016 | Sage et al. |
| 9,427,573 B2 | 8/2016 | Gindele et al. |
| 9,427,574 B2 | 8/2016 | Lee et al. |
| 9,433,783 B2 | 9/2016 | Wei et al. |
| 9,436,481 B2 | 9/2016 | Drew |
| 9,446,245 B2 | 9/2016 | Grill et al. |
| 9,463,324 B2 | 10/2016 | Olson et al. |
| 9,468,755 B2 | 10/2016 | Westlund et al. |
| 9,471,753 B2 | 10/2016 | Kaula et al. |
| 9,480,846 B2 | 11/2016 | Strother et al. |
| 9,492,672 B2 | 11/2016 | Vamos et al. |
| 9,492,675 B2 | 11/2016 | Torgerson et al. |
| 9,492,678 B2 | 11/2016 | Chow |
| 9,498,628 B2 | 11/2016 | Kaemmerer et al. |
| 9,502,754 B2 | 11/2016 | Zhao et al. |
| 9,504,830 B2 | 11/2016 | Kaula et al. |
| 9,522,282 B2 | 12/2016 | Chow et al. |
| 9,592,389 B2 | 3/2017 | Moffitt |
| 9,610,449 B2 | 4/2017 | Kaula et al. |
| 9,615,744 B2 | 4/2017 | Denison et al. |
| 9,623,257 B2 | 4/2017 | Olson et al. |
| 9,636,497 B2 | 5/2017 | Bradley et al. |
| 9,643,004 B2 | 5/2017 | Gerber |
| 9,653,935 B2 | 5/2017 | Cong et al. |
| 9,656,074 B2 | 5/2017 | Simon et al. |
| 9,656,076 B2 | 5/2017 | Trier et al. |
| 9,656,089 B2 | 5/2017 | Yip et al. |
| 9,675,809 B2 | 6/2017 | Chow |
| 9,687,649 B2 | 6/2017 | Thacker |
| 9,707,405 B2 | 7/2017 | Shishilla et al. |
| 9,713,706 B2 | 7/2017 | Gerber |
| 9,717,900 B2 | 8/2017 | Swoyer et al. |
| 9,724,526 B2 | 8/2017 | Strother et al. |
| 9,731,116 B2 | 8/2017 | Chen |
| 9,737,704 B2 | 8/2017 | Wahlstrand et al. |
| 9,744,347 B2 | 8/2017 | Chen et al. |
| 9,750,930 B2 | 9/2017 | Chen |
| 9,757,555 B2 | 9/2017 | Novotny et al. |
| 9,764,147 B2 | 9/2017 | Torgerson |
| 9,767,255 B2 | 9/2017 | Kaula et al. |
| 9,776,002 B2 | 10/2017 | Parker et al. |
| 9,776,006 B2 | 10/2017 | Parker et al. |
| 9,776,007 B2 | 10/2017 | Kaula et al. |
| 9,782,596 B2 | 10/2017 | Vamos et al. |
| 9,814,884 B2 | 11/2017 | Parker et al. |
| 9,821,112 B2 | 11/2017 | Olson et al. |
| 9,827,415 B2 | 11/2017 | Stevenson et al. |
| 9,827,424 B2 | 11/2017 | Kaula et al. |
| 9,833,614 B1 | 12/2017 | Gliner |
| 9,844,661 B2 | 12/2017 | Franz et al. |
| 9,849,278 B2 | 12/2017 | Spinelli et al. |
| 9,855,438 B2 | 1/2018 | Parramon et al. |
| 9,872,988 B2 | 1/2018 | Kaula et al. |
| 9,878,165 B2 | 1/2018 | Wilder et al. |
| 9,878,168 B2 | 1/2018 | Shishilla et al. |
| 9,882,420 B2 | 1/2018 | Cong et al. |
| 9,884,198 B2 | 2/2018 | Parker |
| 9,889,292 B2 | 2/2018 | Gindele et al. |
| 9,889,293 B2 | 2/2018 | Siegel et al. |
| 9,889,306 B2 | 2/2018 | Stevenson et al. |
| 9,895,532 B2 | 2/2018 | Kaula et al. |
| 9,899,778 B2 | 2/2018 | Hanson et al. |
| 9,901,284 B2 | 2/2018 | Olsen et al. |
| 9,901,740 B2 | 2/2018 | Drees et al. |
| 9,907,476 B2 | 3/2018 | Bonde et al. |
| 9,907,955 B2 | 3/2018 | Bakker et al. |
| 9,907,957 B2 | 3/2018 | Woods et al. |
| 9,924,904 B2 | 3/2018 | Cong et al. |
| 9,931,513 B2 | 4/2018 | Kelsch et al. |
| 9,931,514 B2 | 4/2018 | Frysz et al. |
| 9,950,171 B2 | 4/2018 | Johanek et al. |
| 9,974,108 B2 | 5/2018 | Polefko |
| 9,974,949 B2 | 5/2018 | Thompson et al. |
| 9,981,121 B2 | 5/2018 | Seifert et al. |
| 9,981,137 B2 | 5/2018 | Eiger |
| 9,987,493 B2 | 6/2018 | Torgerson et al. |
| 9,993,650 B2 | 6/2018 | Seitz et al. |
| 9,999,765 B2 | 6/2018 | Stevenson |
| 10,004,910 B2 | 6/2018 | Gadagkar et al. |
| 10,016,596 B2 | 7/2018 | Stevenson et al. |
| 10,027,157 B2 | 7/2018 | Labbe et al. |
| 10,045,764 B2 | 8/2018 | Scott et al. |
| 10,046,164 B2 | 8/2018 | Gerber |
| 10,047,782 B2 | 8/2018 | Sage et al. |

(56) References Cited

U.S. PATENT DOCUMENTS

| | | |
|---|---|---|
| 10,052,490 B2 | 8/2018 | Kaula et al. |
| 10,065,044 B2 | 9/2018 | Sharma et al. |
| 10,071,247 B2 | 9/2018 | Childs |
| 10,076,661 B2 | 9/2018 | Wei et al. |
| 10,076,667 B2 | 9/2018 | Kaula et al. |
| 10,083,261 B2 | 9/2018 | Kaula et al. |
| 10,086,191 B2 | 10/2018 | Bonde et al. |
| 10,086,203 B2 | 10/2018 | Kaemmerer |
| 10,092,747 B2 | 10/2018 | Sharma et al. |
| 10,092,749 B2 | 10/2018 | Stevenson et al. |
| 10,095,837 B2 | 10/2018 | Corey et al. |
| 10,099,051 B2 | 10/2018 | Stevenson et al. |
| 10,103,559 B2 | 10/2018 | Cottrill et al. |
| 10,109,844 B2 | 10/2018 | Dai et al. |
| 10,118,037 B2 | 11/2018 | Kaula et al. |
| 10,124,164 B2 | 11/2018 | Stevenson et al. |
| 10,124,171 B2 | 11/2018 | Kaula et al. |
| 10,124,179 B2 | 11/2018 | Norton et al. |
| 10,141,545 B2 | 11/2018 | Kraft et al. |
| 10,173,062 B2 | 1/2019 | Parker |
| 10,179,241 B2 | 1/2019 | Walker et al. |
| 10,179,244 B2 | 1/2019 | Lebaron et al. |
| 10,183,162 B2 | 1/2019 | Johnson et al. |
| 10,188,857 B2 | 1/2019 | North et al. |
| 10,195,419 B2 | 2/2019 | Shiroff et al. |
| 10,206,710 B2 | 2/2019 | Kern et al. |
| 10,213,229 B2 | 2/2019 | Chitre et al. |
| 10,220,210 B2 | 3/2019 | Walker et al. |
| 10,226,617 B2 | 3/2019 | Finley et al. |
| 10,226,636 B2 | 3/2019 | Gaddam et al. |
| 10,236,709 B2 | 3/2019 | Decker et al. |
| 10,238,863 B2 | 3/2019 | Gross et al. |
| 10,238,877 B2 | 3/2019 | Kaula et al. |
| 10,244,956 B2 | 4/2019 | Kane |
| 10,245,434 B2 | 4/2019 | Kaula et al. |
| 10,258,800 B2 | 4/2019 | Perryman et al. |
| 10,265,532 B2 | 4/2019 | Carcieri et al. |
| 10,277,055 B2 | 4/2019 | Peterson et al. |
| 10,293,168 B2 | 5/2019 | Bennett et al. |
| 10,328,253 B2 | 6/2019 | Wells |
| 10,363,419 B2 | 7/2019 | Simon et al. |
| 10,369,275 B2 | 8/2019 | Olson et al. |
| 10,369,370 B2 | 8/2019 | Shishilla et al. |
| 10,376,701 B2 | 8/2019 | Kaula et al. |
| 10,448,889 B2 | 10/2019 | Gerber et al. |
| 10,456,574 B2 | 10/2019 | Chen et al. |
| 10,471,262 B2 | 11/2019 | Perryman et al. |
| 10,485,970 B2 | 11/2019 | Gerber et al. |
| 10,493,282 B2 | 12/2019 | Caparso et al. |
| 10,493,287 B2 | 12/2019 | Yoder et al. |
| 10,561,835 B2 | 2/2020 | Gerber |
| 2002/0040185 A1 | 4/2002 | Atalar et al. |
| 2002/0051550 A1 | 5/2002 | Leysieffer |
| 2002/0051551 A1 | 5/2002 | Leysieffer et al. |
| 2002/0140399 A1 | 10/2002 | Echarri et al. |
| 2002/0177884 A1 | 11/2002 | Ahn et al. |
| 2003/0023296 A1* | 1/2003 | Osypka ............... A61N 1/056 607/122 |
| 2003/0028231 A1 | 2/2003 | Partridge et al. |
| 2003/0114899 A1 | 6/2003 | Woods et al. |
| 2003/0212440 A1 | 11/2003 | Boveja |
| 2004/0087984 A1 | 5/2004 | Kupiecki et al. |
| 2004/0098068 A1 | 5/2004 | Carbunaru et al. |
| 2004/0172115 A1 | 9/2004 | Miazga et al. |
| 2004/0210290 A1 | 10/2004 | Omar-Pasha |
| 2004/0230282 A1 | 11/2004 | Cates et al. |
| 2004/0250820 A1 | 12/2004 | Forsell |
| 2004/0267137 A1 | 12/2004 | Peszynski et al. |
| 2005/0004619 A1 | 1/2005 | Wahlstrand et al. |
| 2005/0004621 A1 | 1/2005 | Boveja et al. |
| 2005/0021108 A1 | 1/2005 | Klosterman et al. |
| 2005/0075693 A1 | 4/2005 | Toy et al. |
| 2005/0075694 A1 | 4/2005 | Schmeling et al. |
| 2005/0075696 A1 | 4/2005 | Forsberg et al. |
| 2005/0075697 A1 | 4/2005 | Olson et al. |
| 2005/0075698 A1 | 4/2005 | Phillips et al. |
| 2005/0075699 A1 | 4/2005 | Olson et al. |
| 2005/0075700 A1 | 4/2005 | Schommer et al. |
| 2005/0104577 A1 | 5/2005 | Matei et al. |
| 2005/0187590 A1 | 8/2005 | Boveja et al. |
| 2006/0041295 A1 | 2/2006 | Osypka |
| 2006/0074412 A1 | 4/2006 | Zerfas et al. |
| 2006/0095078 A1 | 5/2006 | Tronnes et al. |
| 2006/0122676 A1 | 6/2006 | Ko et al. |
| 2006/0142822 A1 | 6/2006 | Tulgar |
| 2006/0149345 A1 | 7/2006 | Boggs et al. |
| 2006/0200205 A1 | 9/2006 | Haller |
| 2006/0206166 A1 | 9/2006 | Weiner |
| 2007/0032836 A1 | 2/2007 | Thrope et al. |
| 2007/0239224 A1 | 10/2007 | Bennett et al. |
| 2007/0255368 A1 | 11/2007 | Bonde et al. |
| 2007/0255369 A1 | 11/2007 | Bonde et al. |
| 2007/0265675 A1 | 11/2007 | Lund et al. |
| 2007/0293914 A1 | 12/2007 | Woods et al. |
| 2008/0065182 A1 | 3/2008 | Strother et al. |
| 2008/0103570 A1 | 5/2008 | Gerber et al. |
| 2008/0132969 A1 | 6/2008 | Bennett et al. |
| 2008/0154335 A1 | 6/2008 | Thrope et al. |
| 2008/0161874 A1 | 7/2008 | Bennett et al. |
| 2008/0183236 A1 | 7/2008 | Gerber |
| 2008/0183257 A1 | 7/2008 | Imran et al. |
| 2009/0012592 A1 | 1/2009 | Buysman et al. |
| 2010/0076254 A1 | 3/2010 | Jimenez et al. |
| 2010/0076534 A1 | 3/2010 | Mock |
| 2010/0100158 A1 | 4/2010 | Thrope et al. |
| 2010/0121421 A1* | 5/2010 | Duncan ............... A61N 1/05 607/116 |
| 2010/0160997 A1 | 6/2010 | Johnson et al. |
| 2010/0256696 A1 | 10/2010 | Schleicher et al. |
| 2011/0251662 A1 | 10/2011 | Griswold et al. |
| 2011/0257701 A1 | 10/2011 | Strother et al. |
| 2011/0270269 A1 | 11/2011 | Swoyer et al. |
| 2011/0282416 A1 | 11/2011 | Hamann et al. |
| 2011/0301667 A1 | 12/2011 | Olson et al. |
| 2011/0313427 A1 | 12/2011 | Gindele et al. |
| 2012/0041512 A1 | 2/2012 | Weiner |
| 2012/0046712 A1 | 2/2012 | Woods et al. |
| 2012/0053665 A1 | 3/2012 | Stolz et al. |
| 2012/0095478 A1 | 4/2012 | Wang et al. |
| 2012/0130448 A1 | 5/2012 | Woods et al. |
| 2012/0179221 A1 | 7/2012 | Reddy et al. |
| 2012/0191169 A1 | 7/2012 | Rothstein et al. |
| 2012/0203320 A1 | 8/2012 | DiGiore et al. |
| 2012/0276854 A1 | 11/2012 | Joshi et al. |
| 2012/0276856 A1 | 11/2012 | Joshi et al. |
| 2012/0310317 A1 | 12/2012 | Lund et al. |
| 2012/0330354 A1 | 12/2012 | Kane et al. |
| 2013/0004925 A1 | 1/2013 | Labbe et al. |
| 2013/0006330 A1 | 1/2013 | Wilder et al. |
| 2013/0006331 A1 | 1/2013 | Weisgarber et al. |
| 2013/0018445 A1* | 1/2013 | Sakai ............... A61N 1/0558 607/116 |
| 2013/0018447 A1 | 1/2013 | Ollivier et al. |
| 2013/0023724 A1 | 1/2013 | Allen et al. |
| 2013/0131766 A1 | 5/2013 | Crosby et al. |
| 2013/0150925 A1 | 6/2013 | Vamos et al. |
| 2013/0150936 A1 | 6/2013 | Takahashi |
| 2013/0150939 A1 | 6/2013 | Burnes et al. |
| 2013/0184773 A1 | 7/2013 | Libbus et al. |
| 2013/0197608 A1 | 8/2013 | Eiger |
| 2013/0207863 A1 | 8/2013 | Joshi |
| 2013/0310894 A1 | 11/2013 | Trier |
| 2013/0331909 A1 | 12/2013 | Gerber |
| 2014/0081363 A1* | 3/2014 | Clark ............... A61N 1/0558 607/116 |
| 2014/0128952 A1 | 5/2014 | Jang |
| 2014/0222112 A1 | 8/2014 | Fell |
| 2014/0237806 A1 | 8/2014 | Smith et al. |
| 2014/0277270 A1 | 9/2014 | Parramon et al. |
| 2015/0088227 A1 | 3/2015 | Shishilla et al. |
| 2015/0214604 A1 | 7/2015 | Zhao et al. |
| 2016/0045724 A1 | 2/2016 | Lee et al. |
| 2017/0197079 A1 | 7/2017 | Illegems et al. |
| 2017/0340878 A1 | 11/2017 | Wahlstrand et al. |

(56) References Cited

U.S. PATENT DOCUMENTS

| | | |
|---|---|---|
| 2018/0021587 A1 | 1/2018 | Strother et al. |
| 2018/0036477 A1 | 2/2018 | Olson et al. |
| 2019/0269918 A1 | 9/2019 | Parker |
| 2019/0351244 A1 | 11/2019 | Shishilla et al. |
| 2019/0358395 A1 | 11/2019 | Olson et al. |

FOREIGN PATENT DOCUMENTS

| | | |
|---|---|---|
| AU | 5123800 | 11/2000 |
| CA | 2371378 | 11/2000 |
| CA | 2554676 | 9/2005 |
| CA | 2957962 | 5/2018 |
| DE | 3146182 | 6/1983 |
| EP | 0656218 | 6/1995 |
| EP | 1205004 | 5/2002 |
| EP | 1680182 A1 | 7/2006 |
| EP | 1680182 B1 | 7/2006 |
| EP | 2243509 A1 | 10/2010 |
| ES | 2395128 | 2/2013 |
| HK | 1098715 | 3/2012 |
| JP | 2007268293 | 10/2007 |
| JP | 4125357 | 7/2008 |
| WO | WO 1998/20933 A1 | 5/1998 |
| WO | 9918879 | 4/1999 |
| WO | 9934870 | 7/1999 |
| WO | 9942173 | 8/1999 |
| WO | WO 00/56677 A1 | 3/2000 |
| WO | WO 00/27469 A2 | 5/2000 |
| WO | 0065682 | 11/2000 |
| WO | 0069012 | 11/2000 |
| WO | 0183029 | 11/2001 |
| WO | 0209808 | 2/2002 |
| WO | WO 2003/084433 A3 | 10/2003 |
| WO | 2004021876 | 3/2004 |
| WO | 2004103465 | 12/2004 |
| WO | 2005079295 | 9/2005 |
| WO | 2005081740 | 9/2005 |
| WO | WO 2006/116205 A1 | 11/2006 |
| WO | WO 2007/022180 A1 | 2/2007 |
| WO | WO 2008/021524 A2 | 2/2008 |
| WO | WO 2008/094952 A2 | 8/2008 |
| WO | WO 2008/153726 A2 | 12/2008 |
| WO | WO 2009/102536 A1 | 8/2009 |
| WO | WO 2009/135075 A1 | 11/2009 |
| WO | WO 2010/107751 A2 | 9/2010 |
| WO | WO 2011/059565 A1 | 5/2011 |
| WO | WO 2013/063798 A1 | 5/2013 |
| WO | WO 2013/070490 A1 | 5/2013 |
| WO | WO 2013/156038 A1 | 10/2013 |

OTHER PUBLICATIONS

Bosch, J., et al., Sacral (S3) Segmental Nerve Stimulation as a Treatment for Urge Incontinence in Patients With Detrusor Instability: Results of Chronic Electrical Stimulation Using an Implantable Neural Prosthesis, The Journal of Urology, Aug. 1995, vol. 154, pp. 504-507.
Chartier-Kastler, E., Sacral neuromodulation for treating the symptoms of overactive bladder syndrome and non-obstructive urinary retention:> 10 years of clincial experience, Journal Compilation, BJU International, 2007,101, pp. 417-423.
Ghovanloo, M., et al., A Small Size Large Voltage Compliance Programmable Current Source for Biomedical Implantable Microstimulators, Proceedings of the 25th Annual International Conference of the IEEE EMBS, Sep. 17-21, 2003, pp. 1979-1982.
Tanagho, E., et al., Bladder Pacemaker: Scientific Basis and Clinical Future, Urology, Dec. 1982, vol. 20, No. 6, pp. 614-619.
U.S. Appl. No. 14/827,081, filed Aug. 14, 2015.
U.S. Appl. No. 14/827,108, filed Aug. 14, 2015.
U.S. Appl. No. 14/991,752, filed Jan. 8, 2016.
U.S. Appl. No. 14/827,095, filed Aug. 14, 2015.
U.S. Appl. No. 14/827,067, filed Aug. 14, 2015.
U.S. Appl. No. 14/991,784, filed Jan. 8, 2016.
U.S. Appl. No. 62/101,888, filed Jan. 9, 2015.
U.S. Appl. No. 62/101,899, filed Jan. 9, 2015.
U.S. Appl. No. 62/041,611, filed Aug. 25, 2014.
U.S. Appl. No. 62/038,131, filed Aug. 15, 2014.
U.S. Appl. No. 62/101,897, filed Jan. 9, 2015.
U.S. Appl. No. 62/101,666, filed Jan. 9, 2015.
U.S. Appl. No. 62/101,884, filed Jan. 9, 2015.
U.S. Appl. No. 62/101,782, filed Jan. 9, 2015.
U.S. Appl. No. 62/191,134, filed Jul. 10, 2015.
"Bu-802a: How Does Rising Internal Resistance Affect Performance? Understanding the Importance of Low Conductivity", BatteryUniversity.com, Available Online at https://batteryuniversity.com/learn/article/rising_internal_resistance, Accessed from Internet on: May 15, 2020, 10 pages.
"DOE Handbook: Primer on Lead-Acid Storage Batteries", U.S. Dept. of Energy, Available Online at: htt12s:///www.stan dards.doe.gov/standards- documents/ I 000/1084-bhdbk-1995/@@images/file, Sep. 1995, 54 pages.
"Medical Electrical Equipment—Part 1: General Requirements for Safety", British Standard, BS EN 60601-1:1990-BS5724-1:1989, Mar. 1979, 200 pages.
"Summary of Safety and Effectiveness", Medtronic InterStim System for Urinary Control, Apr. 15, 1999, pp. 1-18.
"The Advanced Bionics PRECISION™ Spinal Cord Stimulator System", Advanced Bionics Corporation, Apr. 27, 2004, pp. 1-18.
"UL Standard for Safety for Medical and Dental Equipment", UL 544, 4th edition, Dec. 30, 1998, 128 pages.
Barnhart et al., "A Fixed-Rate Rechargeable Cardiac Pacemaker", APL Technical Digest, Jan.-Feb. 1970, pp. 2-9.
Benditt et al., "A Combined Atrial/Ventricular Lead for Permanent Dual-Chamber Cardiac Pacing Applications", Chest, vol. 83, No. 6, Jun. 1983, pp. 929-931.
Boyce et al., "Research Related to the Development of an Artificial Electrical Stimulator for the Paralyzed Human Bladder: a Review", The Journal of Urology, vol. 91, No. 1, Jan. 1964, pp. 41-51.
Bradley et al., "Further Experience With the Radio Transmitter Receiver Unit for the Neurogenic Bladder", Journal of Neurosurgery, vol. 20, No. 11, Nov. 1963, pp. 953-960.
Broggi et al., "Electrical Stimulation of the Gasserian Ganglion for Facial Pain: Preliminary Results", Acta Neurochirurgica, vol. 39, 1987, pp. 144-146.
Cameron et al., "Effects of Posture on Stimulation Parameters in Spinal Cord Stimulation", Neuromodulation, vol. 1, No. 4, Oct. 1998, pp. 177-183.
Connelly et al., "Atrial Pacing Leads Following Open Heart Surgery: Active or Passive Fixation?", Pacing and Clinical Electrophysiology, vol. 20, No. 10, Oct. 1997, pp. 2429-2433.
Fischell , "The Development of Implantable Medical Devices at the Applied Physics Laboratory", Johns Hopkins APL Technical Digest, vol. 13 No. 1, 1992, pp. 233-243.
Gaunt et al., "Control of Urinary Bladder Function With Devices: Successes and Failures", Progress in Brain Research, vol. 152, 2006, pp. 1-24.
Helland , "Technical Improvements to be Achieved by the Year 2000: Leads and Connector Technology", Rate Adaptive Cardiac Pacing, Springer Verlag, 1993, pp. 279-292.
Hidefjall , "The Pace of Innovation—Patterns of Innovation in the Cardiac Pacemaker Industry", Linkoping University Press, 1997, 398 pages.
Ishihara et al., "A Comparative Study of Endocardial Pacemaker Leads", Cardiovascular Surgery, Nagoya Ekisaikai Hospital, 1st Dept. of Surgery, Nagoya University School of Medicine, 1981, pp. 132-135.
Jonas et al., "Studies on the Feasibility of Urinary Bladder Evacuation by Direct Spinal Cord Stimulation. I. Parameters of Most Effective Stimulation", Investigative urology, vol. 13, No. 2, 1975, pp. 142-150.
Kakuta et al., "In Vivo Long Term Evaluation of Transcutaneous Energy Transmission for Totally Implantable Artificial Heart", ASAIO Journal, Mar.-Apr. 2000, pp. 1-2.

(56) References Cited

OTHER PUBLICATIONS

Kester et al., "Voltage-to-Frequency Converters", Available Online at: https://www.analog.com/media/cn/training-seminars/tutorials/MT-028.pdf, 7 pages.

Lazorthes et al., "Chronic Stimulation of the Gasserian Ganglion for Treatment of Atypical Facial Neuralgia", Pacing and Clinical Electrophysiology, vol. 10, Jan.-Feb. 1987, pp. 257-265.

Lewis et al., "Early Clinical Experience with the Rechargeable Cardiac Pacemaker", The Annals of Thoracic Surgery, vol. 18, No. 5, Nov. 1974, pp. 490-493.

Love et al., "Experimental Testing of a Permanent Rechargeable Cardiac Pacemaker", The Annals of Thoracic Surgery, vol. 17, No. 2, Feb. 1, 1974, pp. 152-156.

Love, "Pacemaker Troubleshooting and Follow-up", Clinical Cardiac Pacing, Defibrillation, and Resynchronization Therapy, Chapter 24, 2007, pp. 1005-1062.

Madigan et al., "Difficulty of Extraction of Chronically Implanted Tined Ventricular Endocardial Leads", Journal of the American College of Cardiology, vol. 3, No. 3, Mar. 1984, pp. 724-731.

Meglio, "Percutaneously Implantable Chronic Electrode for Radiofrequency Stimulation of the Gasserian Ganglion. A Perspective in the Management of Trigeminal Pain", Acta Neurochirurgica, vol. 33, 1984, pp. 521-525.

Meyerson, "Alleviation of Atypical Trigeminal Pain by Stimulation of the Gasserian Ganglion via an Implanted Electrode", Acta Neurochirurgica Supplementum, vol. 30, 1980, pp. 303-309.

Mitamura et al., "Development of Transcutaneous Energy Transmission System", Available Online at https://www.researchgate.net/publication/312810915 Ch.28, Jan. 1988, pp. 265-270.

Nakamura et al., "Biocompatibility and Practicality Evaluations of Transcutaneous Energy Transmission Unit for the Totally Implantable Artifical Heart System", Journal of Artificial Organs, vol. 27, No. 2, 1998, pp. 347-351.

Nashold et al., "Electromicturition in Paraplegia. Implantation of a Spinal Neuroprosthesis", Arch Surg., vol. 104, Feb. 1972, pp. 195-202.

Painter et al., "Implantation of an Endocardial Tined Lead to Prevent Early Dislodgement", The Journal of Thoracic and Cardiovascular Surgery, vol. 77, No. 2, Feb. 1979, pp. 249-251.

Perez, "Lead-Acid Battery State of Charge vs. Voltage", Available Online at http://www.rencobattery.com/resources/SOC vs-Voltage.pdf, Aug.-Sep. 1993, 5 pages.

Schaldach et al., "A Long-Lived, Reliable, Rechargeable Cardiac Pacemaker", Engineering in Medicine, vol. 1: Advances in Pacemaker Technology, 1975, 34 pages.

Scheuer-Leeser et al., "Polyurethane Leads: Facts and Controversy", Pace, vol. 6, Mar.-Apr. 1983, pp. 454-458.

Smith, "Changing Standards for Medical Equipment", UL 544 and UL 187 vs. UL 2601 ("Smith"), 2002, 8 pages.

Tanagho, "Neuromodulation and Neurostimulation: Overview and Future Potential", Translational Androl Urol, vol. 1, No. 1, 2012, pp. 44-49.

Torres et al., "Electrostatic Energy-Harvesting and Battery-Charging CMOS System Prototype", Available Online at : http://rincon mora.gatech.edu/12ublicat/jrnls/tcasi09_hrv_sys.pdf, pp. 1-10.

Young, "Electrical Stimulation of the Trigeminal Nerve Root for the Treatment of Chronic Facial Pain", Journal of Neurosurgery, vol. 83, No. 1, Jul. 1995, pp. 72-78.

\* cited by examiner

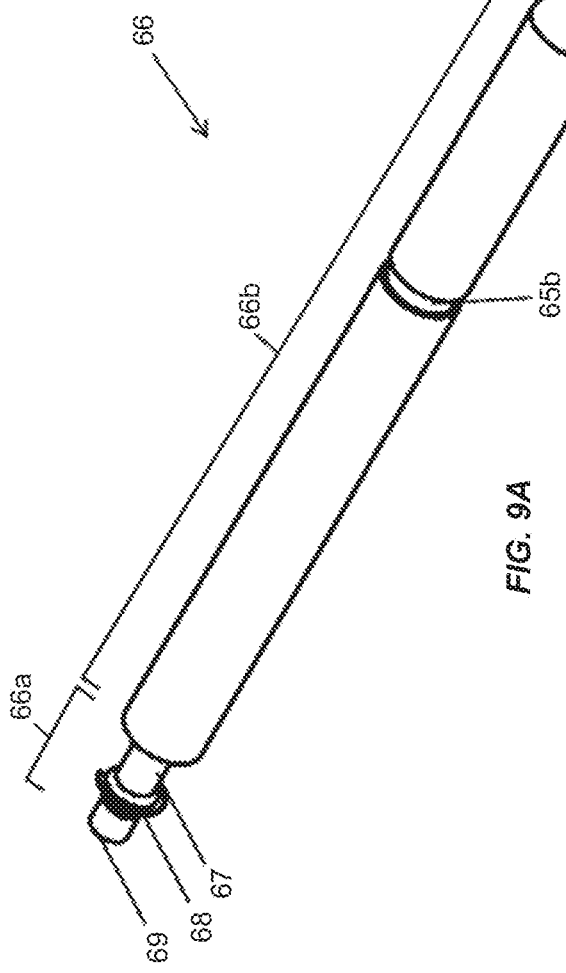
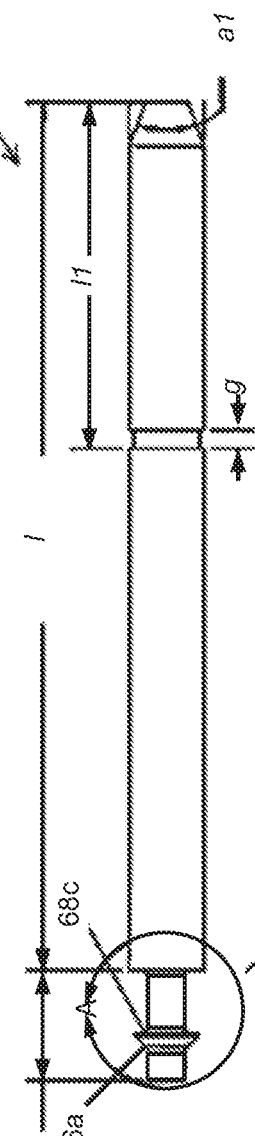
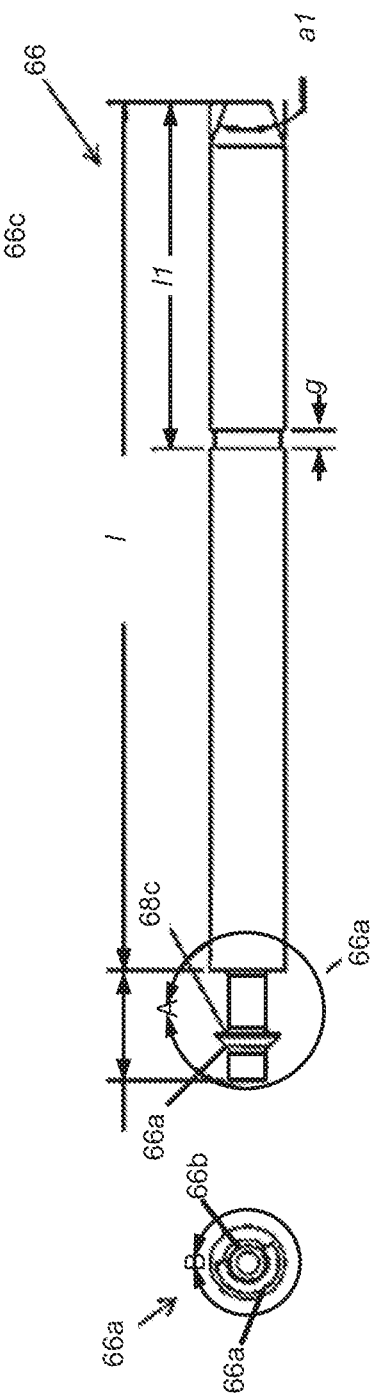
FIG. 9A
FIG. 9B
FIG. 9C

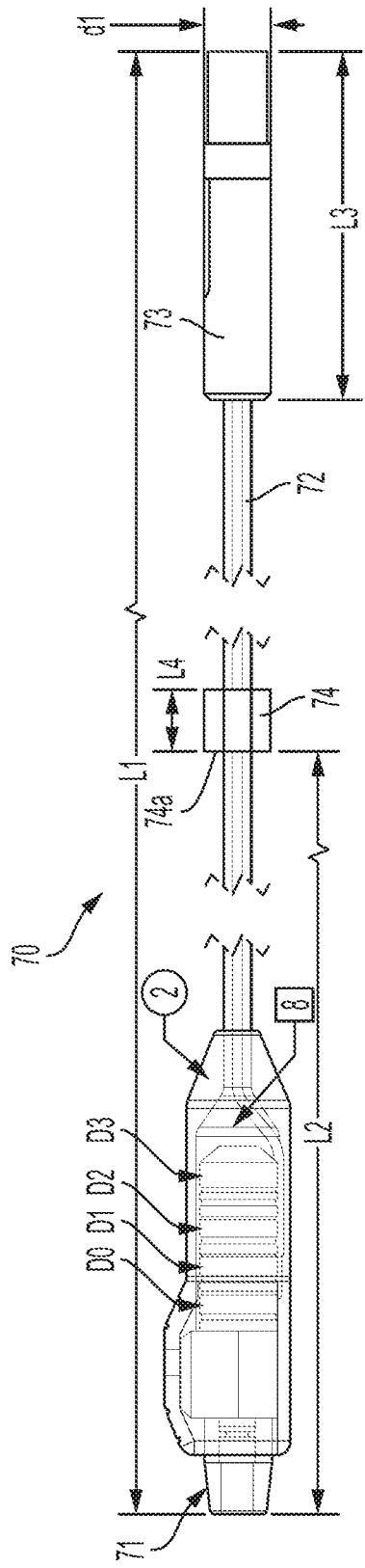
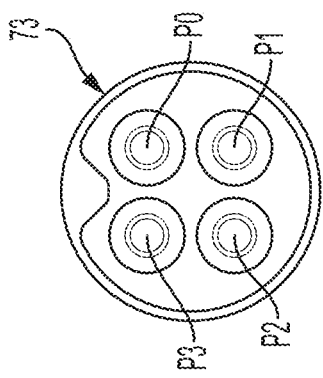
FIG. 12B
FIG. 11
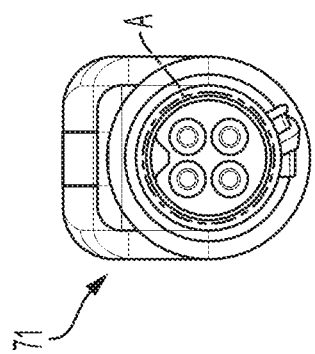
FIG. 12A

FIG. 13B SECTION B-B

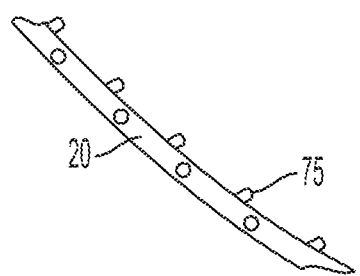
FIG. 18
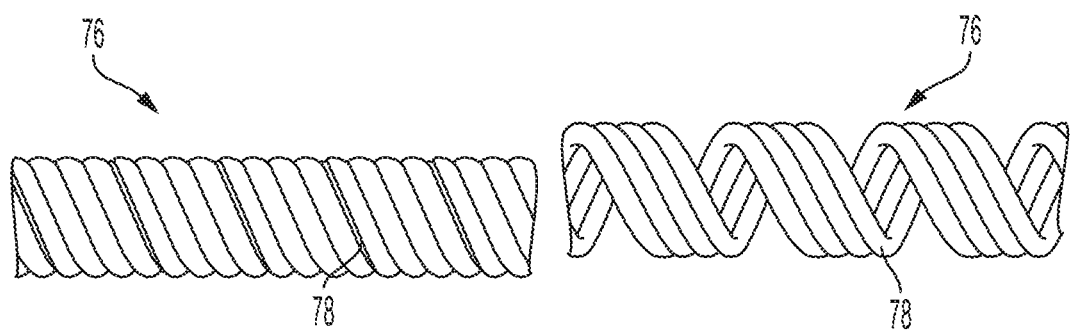
FIG. 19A  FIG. 19B
FIG. 19C
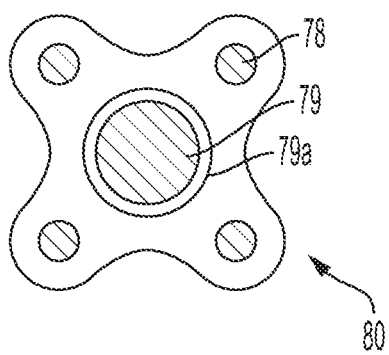 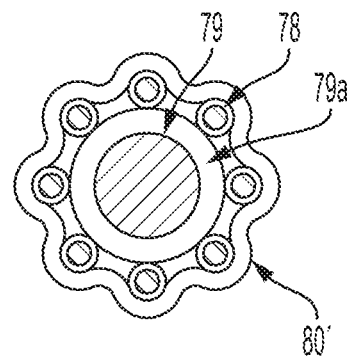
FIG. 20A  FIG. 20B

NEUROSTIMULATION LEADS FOR TRIAL NERVE STIMULATION AND METHODS OF USE

CROSS-REFERENCES TO RELATED APPLICATIONS

This application claims the benefit of U.S. Provisional Application No. 62/633,806, filed on Feb. 22, 2018, and entitled "NEUROSTIMULATION LEADS FOR TRIAL NERVE STIMULATION AND METHODS OF USE," the entirety of which is hereby incorporated by reference herein.

The present application is related to U.S. Non-Provisional application Ser. No. 15/431,475, entitled "Neurostimulation Lead for Trial Nerve Stimulation and Methods of Use," filed Feb. 13, 2017 and U.S. Non-Provisional application Ser. No. 14/827,081, entitled External Pulse Generator Device and Associated Methods for Trial Nerve Stimulation" filed on Aug. 14, 2015, the entire contents of which are incorporated herein by reference in its entirety for all purposes.

BACKGROUND OF THE INVENTION

Treatments with implanted neurostimulation systems have become increasingly more common in recent years. While such systems have shown promise in treating a number of chronic conditions, effectiveness of treatment may vary considerably between patients and viability of treatment can be difficult to determine before implantation. Although conventional methods of implantation often utilize preliminary testing with a temporary, partially implanted neurostimulation systems to assess viability of treatment, such systems may not provide an accurate representation of treatment with a fully implanted device. Many such temporary partially implanted systems may not operate in the same manner as their fully implanted counterparts due to differences between pulse generators or changes in position of the neurostimulation leads due to regression or migration of the lead. Regression of a temporary lead or tined lead can also cause failure of an electrical connection of the lead or infection of a secondary incision site. Therefore, it is desirable to provide methods and devices for providing neurostimulation leads that provide consistent treatment outcomes by improved leads and lead connections, improved implantation and removal, and more seamless conversion from a trial system to a long-term fully implanted neurostimulation system.

BRIEF SUMMARY OF THE INVENTION

The present invention relates to neurostimulation treatment systems, and in particular a neurostimulation leads for nerve stimulation trials or evaluations as well as and permanently implanted systems.

In one aspect, the invention pertains to a neurostimulation lead that includes a retention feature between a conductor and a proximal contact connector. In some embodiments, the lead includes at least one coiled conductor extending from a proximal portion of the neurostimulation lead to a distal electrode on a distal portion of the neurostimulation lead and a proximal contact connector electrically coupled with the at least one coiled conductor and configured for electrically connecting the lead to a pulse generator or to an external cable which then connects to the pulse generator. The proximal contact connector includes a distal retention flange and a reduced profile coupling portion proximal of the distal retention flange, wherein one or more coils of the conductor are positioned along the coupling portion and fixedly attached thereto. One or more coils engage the proximal facing surface of the retention flange so as to resist tension between the coiled lead and proximal contact connector and maintain integrity of electrical connection between the coiled conductor and the coupling portion of the proximal contact connector.

In some embodiments, the retention flange includes a distal facing ramp surface extending at least partly about the circumference of the proximal contact connector to facilitate assembly of the coiled conductor with the proximal contact connector. In some embodiments, the retention flange includes an open notch portion having a reduced radius as compared to a remainder of the flange so as to allow the coiled conductor to be screwed onto the coupling portion past the flange. In some embodiments, the open notch portion is between 90 to 160 degrees about the circumference. The ramped surface of the retention flange is ramped, for example at an angle between 30 and 60 degrees, typically about 45 degrees to facilitate feeding of the coiled lead upon the connector. The proximal facing retention surface of the retention flange extends substantially perpendicular to a longitudinal axis of the proximal connector.

In some embodiments, the coiled conductor is fixedly attached and electrically coupled to the coupling portion of the proximal contact connector by soldering or laser welding. The proximal contact connector can include a proximal portion that is elongate to facilitate connection of the lead to a pulse generator and includes a proximal opening to facilitate introduction of a stylet through an open lumen of the lead.

In some embodiments, the retention flange is configured to withstand a tensile force of at least 5 N. In the application described herein, the retention flange is configured to withstand a minimum tensile force of 10-12 N. It is appreciated that the desired minimum tensile force can vary according to the properties of a particular lead or application.

In some embodiments, the lead further includes an outer insulator coating disposed on the coiled conductor along at least an intermediate portion of the neurostimulation lead between the proximal portion and the distal electrode, wherein the distal electrode is defined by an exposed portion of the coiled conductor without the outer insulator coating. In some embodiments, the neurostimulation lead has substantially the same outer diameter along the coiled conductor and the proximal contact connector to facilitate passage of the lead through a foramen needle. In some embodiments, a majority of the coiled conductor is closed wound at a first pitch. The coiled conductor includes one or more open coiled portions wound at a second pitch, wherein the one or more open coiled portions are positioned at distances from the distal electrode that correspond to a length of one or more foramen needles.

In some embodiments, the neurostimulation lead includes a single electrode has a surface area within a range of about 0.01 in$^2$ to 0.1 in$^2$. The length or surface area of the first electrode can be configured to correspond to a dimension of an electrode portion of an implantable neurostimulation lead to be placed after percutaneous nerve evaluation. Such neurostimulation leads can be utilized for sacral nerve stimulation, in particular the lead is suited for use as a trial stimulation lead for percutaneous nerve evaluation.

In some embodiments, the neurostimulation lead includes one or more additional conductors extending from the proximal portion of the neurostimulation lead to one or more additional electrodes along the distal portion of the neurostimulation lead. The one or more additional coiled conductors can be electrically coupled and fixedly attached to the coupling portion of the proximal contact connector and one or more coils of each of the one or more additional coiled conductors are disposed proximal of the retention flange. In some embodiments, the coiled conductor and the one or more additional conductors are defined by a multi-ribbon conductor. In other embodiments, a multi-electrode lead can include multiple insulated conductors wound about a tube having a central lumen.

In any of the neurostimulation leads described herein, the conductor or lead body can include a coating of the coiled conductor comprised of a textured surface configured to provide improved retention along at least the one or more retention features. In some embodiments, the coating includes a barbed surface having a plurality of barbs oriented to inhibit movement of the neurostimulation lead.

In some embodiments, a neurostimulation lead defined by one or more coiled conductors includes an open coil pitch along at least a portion of an implantable length of the lead so as to resist migration of the lead. The open coil pitch can be of the same diameter as the closed coiled portions. Such open coiled portions can be formed during winding of the lead, as opposed to being formed by stretching or elongating closed wound portions, so as to avoid plastic deformation of the conductor.

In another aspect, a neurostimulation lead can include one or more anchors attached thereto. In some embodiments, such leads can include a retractable anchoring feature at a distal end, the anchoring feature attached to an elongate member extending through the proximal contact connector such that retraction of the elongate member retracts the distal anchor into a central lumen of the coiled conductor. In other embodiments, a lead can include a bioabsorbable anchor disposed at a distal end or adjacent the distal electrode, the anchor being configured to absorb after expiration of the trial period to allow ready removal of the lead. In some embodiments, the bioabsorbable anchor includes a radiopaque marker that remains within the body after the anchor absorbs to allow positioning of an electrode of a permanently implanted lead at the same location as the distal electrode of the lead. It is appreciated that these anchoring features are applicable to any type of lead (e.g., coiled, non-coiled, single electrode, multi-electrode) and for any application.

In another aspect, a neurostimulation lead having one or more coiled conductors can include a helical tined anchor configured to attach to the coiled conductor. In some embodiments, the helical tined anchor is wound at a same pitch as a portion of the conductor to which the anchor is attached. The helical tined anchor is formed of any suitable material (e.g. metal, polymer). In some embodiments, the anchor is formed of Nitinol and formed by heat setting so that the tines extend outward from the lead body when attached. In some embodiments, the helical tined anchor is configured to attach to an outer surface of a closed wound portion of the lead along or adjacent the distal electrode. In other embodiments, the helical tined anchor configured to attach to an interior portion of an open coil pitch portion of the coiled conductor such that the tines extend outward from the lead. In some embodiment, the helical tined anchor is configured to attach to a distal end of the lead and includes a distal atraumatic tip to provide an end stop for a stylet inserted within the coiled conductor.

In another aspect, methods of assembling a neurostimulation lead are provided herein. Such methods include assembly of trial leads, particularly PNE leads. Such methods can include: feeding at least one coiled conductor over a distal retention flange of a proximal contact connector so as to position one or more coils of the coiled conductor along a reduced profile coupling portion of the proximal contact connector proximal of the distal retention flange and electrically coupling and fixedly attaching the coiled conductor to the coupling portion by soldering or welding. Such methods further include engaging a proximal facing surface of the distal retention flange with a portion of the one or more coils disposed proximal of the retention flange so as to withstand tensile forces applied by tension in the lead, thereby maintaining the integrity of the electrical connection between the coiled conductor and the proximal contact connector. In some embodiments, a cover or shrink tube is advanced over the interface of the coiled conductor and the proximal contact connector for protection.

In some embodiments, the methods of assembling neurostimulation leads can include attaching one or more anchoring features, the one or more anchoring features including any of a helical anchor disposed along an outer surface of a closed wound portion of the lead, a helical anchor disposed within an open coil pitch portion of the lead, a retractable anchor that retracts into a central lumen of the lead, a bioabsorbable anchor that absorbs after a duration of a trial period, a bioabsorbable lead having a radiopaque marker that remains within the body after the anchor is dissolved.

In another aspect, a lead extension is provided herein. Such a lead extension can include a distal connector and proximal connector coupled via an extension cable. The distal connector is configured for electrically coupling with a fully implanted lead. The proximal connector is configured for coupling with an external pulse generator or intervening connection. The proximal connector is dimensioned for passage through a tool or cannula tunneled from a first incision area of a body of a patient and through a second incision outside the patient's body; an extension cable electrically coupling the distal connector with the proximal connector; and a regression stopper disposed on the extension cable between the proximal connector and the distal connector and configured to prevent regression of the proximal connector into a patient's body through the second incision, wherein the regression stopper is dimensioned for passage through the tunneled tool or cannula along with the proximal connector. In some embodiments, the regression stopper has a distal facing surface that is substantially perpendicular to a longitudinal axis of the extension cable so as to interface with a skin of the patient or associated pad or gauze thereon so as to inhibit regression of the lead through the second incision. In some embodiments, the regression stopper is substantially cylindrical in shape, although it is appreciated various other shapes can be used. In some embodiments, the regression stop can be adjustable or removable, or configured to attach to a larger regression stopper feature.

In another aspect, methods of utilizing such a lead extension are provided. Such methods can include: implanting a neurostimulation lead in a body of a patient such that a proximal end of the lead is disposed at a first incision area; tunneling from the first incision area to a second incision; connecting a distal connector of the lead extension at the first incision area and implanting the distal connector at the first incision area, the distal connector being electrically coupled with a proximal connector of the lead extension via an extension cable including a regression stopper; and passing a proximal connector and the regression stopper through a tool or cannula tunneled from the first incision and through the second incision outside the patient's body. The tool or cannula are then removed. Engaging, with the regression stopper, an outer skin of the patient or a pad or gauze disposed thereon inhibit regression of the lead into the patient during a trial period or during explant of the lead extension. This prevents infection of the second incision site and facilitates removal of the lead extension after the trial.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

FIGS. 9A-9C illustrate perspective, front and side views, respectively, of a proximal contact connector of the neurostimulation lead of FIG. 8A.

FIG. 11-13B illustrate several views of an extension cable having a regression stopper, in accordance with some embodiments.

FIG. 18 illustrates an anchoring feature for use in a neurostimulation lead in accordance with some embodiments.

FIGS. 19A-19C illustrate a closed coil and open coil design of multi-electrode neurostimulation leads defined by a multi-conductor ribbon, such as that shown in the cross-section of FIG. 19C, in accordance with some embodiments.

FIGS. 20A-20B illustrate cross-sections of multi-conductor designs having multiple conductors arranged about a central core or conduit for use in multi-electrode neurostimulation leads in accordance with some embodiments.

DETAILED DESCRIPTION OF THE INVENTION

Neurostimulation has been used for many years to treat a variety of conditions, from chronic pain, to erectile dysfunction and various urinary dysfunctions. While neurostimulation has proven effective in many applications, effective therapy often relies on consistently delivering therapeutic activation by one or more neurostimulation electrodes to particular nerves or targeted regions with a pulse generator. In recent years, fully implantable neurostimulation have become increasingly more commonplace. Although such implantable systems provide patients with greater freedom and mobility, the neurostimulation electrodes of such systems are more difficult to adjust once they are implanted. The neurostimulation electrodes are typically provided on a distal end of an implantable lead that is advanced through a tunnel formed in a patient tissue.

Figure 1:
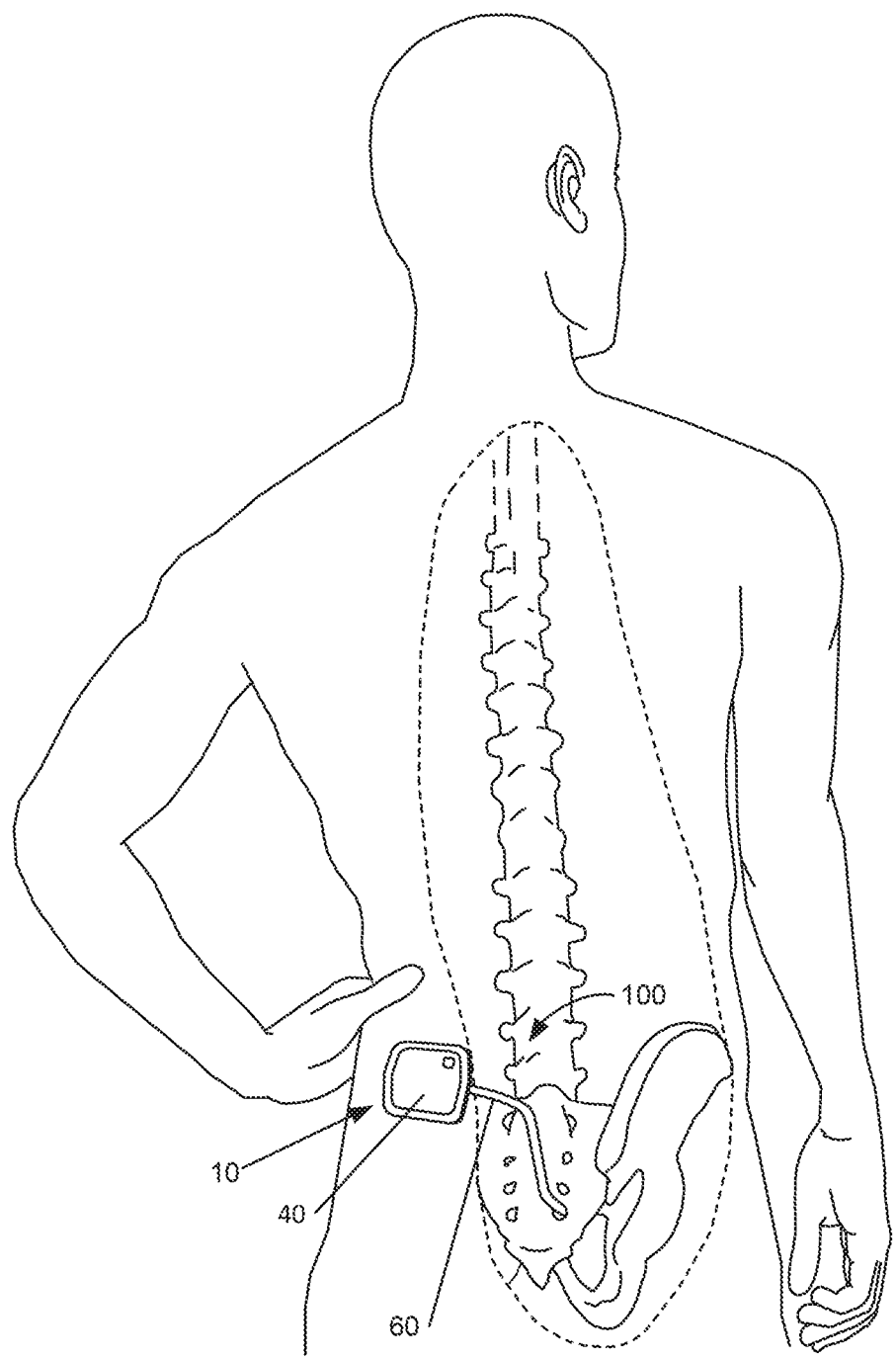
FIG. 1 is a schematic illustration of a trial neurostimulation system having a partially implanted lead extending to an EPG patch adhered to the skin of the patient, in accordance with some embodiments of the invention.

FIG. 1 schematically illustrates a use of a trial neurostimulation system utilizing an EPG affixation device, in accordance with aspect of the invention. Such a trial neurostimulation system can be used to assess viability of a fully implantable neurostimulation system. Implantable neurostimulation systems can be used in treating patients with, for example, chronic, severe, refractory neuropathic pain originating from peripheral nerves or various urinary and bowel dysfunctions. Implantable neurostimulation systems can be used to either stimulate a target peripheral nerve or the posterior epidural space of the spine. An implantable neurostimulation system includes an implanted pulse generator, typically implanted in a lower back region. In some embodiments, the pulse generator can generate one or more non-ablative electrical pulses that are delivered to a nerve to control pain or cause some other desired effect. In some applications, the pulses having a pulse amplitude of between 0-1,000 mA, 0-100 mA, 0-50 mA, 0-25 mA, and/or any other or intermediate range of amplitudes may be used. One or more of the pulse generators can include a processor and/or memory adapted to provide instructions to and receive information from the other components of the implantable neurostimulation system. The processor can include a microprocessor, such as a microprocessor from Intel® or Advanced Micro Devices, Inc.®, or the like. An implantable pulse generator may implement an energy storage feature, such as one or more capacitors or a battery, and typically includes a wireless charging unit.

The electrical pulses generated by the pulse generator are delivered to one or more nerves and/or to a target location via one or more leads that include one or more neurostimulation electrodes at or near the distal end. The leads can have a variety of shapes, can be a variety of sizes, and can be made from a variety of materials, which size, shape, and materials can be dictated by the application or other factors. In some applications, the leads may be implanted to extend along the spine or through one of the foramen of the sacrum, such as shown in FIG. 1, such as in sacral nerve stimulation. In other applications, the leads may be implanted in a peripheral portion of the patient's body, such as in the arms or legs, and can be configured to deliver one or more electrical pulses to the peripheral nerve such as may be used to relieve chronic pain.

One or more properties of the electrical pulses can be controlled via a controller of the implanted pulse generator. In some embodiments, these properties can include, for example, the frequency, strength, pattern, duration, or other aspects of the timing and magnitude of the electrical pulses. These properties can include, for example, a voltage, a current, or the like. This control of the electrical pulses can include the creation of one or more electrical pulse programs, plans, or patterns, and in some embodiments, this can include the selection of one or more pre-existing electrical pulse programs, plans, or patterns. In the embodiment depicted in FIG. 1, the implantable neurostimulation system 100 includes a controller in the implantable pulse generator having one or more pulse programs, plans, or patterns and/or to select one or more of the created pulse programs, plans, or patterns.

Sacral neuromodulation (SNM), also known as sacral nerve stimulation (SNS), is defined as the delivery of mild electrical pulses to the sacral nerve to modulate the neural pathways controlling bladder and rectal function. This policy addresses use of SNM in the treatment of urinary or fecal incontinence, urinary or fecal nonobstructive retention, or chronic pelvic pain in patients with intact neural innervation of the bladder and/or rectum.

Treatment using SNM, also known as SNS, is one of several alternative modalities for patients with fecal incontinence or overactive bladder (urge incontinence, significant symptoms of urgency-frequency) or nonobstructive urinary retention who have failed behavioral (e.g., prompted voiding) and/or pharmacologic therapies. Urge incontinence is defined as leakage of urine when there is a strong urge to void. Urgency-frequency is an uncontrollable urge to urinate, resulting in very frequent small volumes. Urinary retention is the inability to completely empty the bladder of urine. Fecal incontinence is the inability to control bowel movements resulting in unexpected leakage of fecal matter.

The SNM device consists of an implantable pulse generator that delivers controlled electrical impulses. This pulse generator is attached to wire leads that connect to the sacral nerves, most commonly the S3 nerve root. Two external components of the system help control the electrical stimulation. A patient remote control may be kept by the patient and can be used to control any of the variety of operational aspects of the EPG and its stimulation parameters. In one such embodiment, the patient remote control may be used to turn the device on or return the EPG to a hibernation state or to adjust stimulation intensity. A console programmer is kept by the physician and used to adjust the settings of the pulse generator.

In a conventional approach, prior to implantation of the permanent device, patients undergo an initial testing phase to estimate potential response to treatment. The first type of testing developed was percutaneous nerve evaluation (PNE). This procedure is done under local anesthesia, using a test needle to identify the appropriate sacral nerve(s). Once identified, a temporary wire lead is inserted through the test needle and left in place for 4 to 7 days. This lead is connected to an external stimulator, which can be carried by patients in their pocket, secured against the skin under surgical dressings, or worn in a belt. The results of this test phase are used to determine whether patients are appropriate candidates for the permanent implanted device. For example, for overactive bladder, if patients show a 50 percent or greater reduction in symptom frequency, they are deemed eligible for the permanent device.

The second type of testing is a 2-stage surgical procedure. In Stage 1, a quadripolar-tined lead is implanted (stage 1). The testing phase can last as long as several weeks, and if patients show a specified reduction in symptom frequency, they can proceed to Stage 2 of the surgery, which is permanent implantation of the neuromodulation device. The 2-stage surgical procedure has been used in various ways. These include its use instead of PNE, for patients who failed PNE, for patients with an inconclusive PNE, or for patients who had a successful PNE to further refine patient selection.

In one aspect, the duration of battery life of the EPG is at least four weeks for a tined lead at nominal impedance (e.g. about 1200 Ohms), an amplitude of about 4.2 mA, and a pulse width of about 210 us, or the duration of battery life can be at least seven days for a PNE lead. In some embodiments, the battery is rechargeable and can be recharged by coupling the battery with a standard 120 V wall outlet, and may optionally utilize the same power cables or adapter as used by other system components (e.g. clinician programmer). Typically, the EPG is current controlled. The EPG can be configured with a pulse width between 60-450 µs, a maximum stimulation rate between 2 and 130 Hz, a maximum amplitude between 0 and 12.5 mA, a stimulation waveform that is biphasic charge-balanced asymmetric, minimum amplitude steps of about 0.05 mA, continuous or cycling operating modes, a set number of neurostimulation programs (e.g. two programs), ramping capability, and optional alert built into the EPG.

The permanent device is implanted under local or general anesthesia. An incision is made over the lower back and the electrical leads are placed in contact with the sacral nerve root(s). The wire leads are extended underneath the skin to a pocket incision where the pulse generator is inserted and connected to the wire leads. Following implantation, the physician programs the pulse generator to the optimal settings for that patient.

One example of a common process for treating bladder dysfunction is to employ a trial period of sacral neuromodulation with either a percutaneous lead or a fully implanted lead in patients that meet all of the following criteria: (1) a diagnosis of at least one of the following: urge incontinence; urgency-frequency syndrome; non-obstructive urinary retention; (2) there is documented failure or intolerance to at least two conventional therapies (e.g., behavioral training such as bladder training, prompted voiding, or pelvic muscle exercise training, pharmacologic treatment for at least a sufficient duration to fully assess its efficacy, and/or surgical corrective therapy); (3) the patient is an appropriate surgical candidate; and (4) incontinence is not related to a neurologic condition.

Permanent implantation of a sacral neuromodulation device may be considered medically necessary in patients who meet all of the following criteria: (1) all of the criteria (1) through (4) in the previous paragraph are met; and (2) trial stimulation period demonstrates at least 50% improvement in symptoms over a period of at least one week.

Other urinary/voiding applications of sacral nerve neuromodulation are considered investigational, including but not limited to treatment of stress incontinence or urge incontinence due to a neurologic condition, e.g., detrusor hyperreflexia, multiple sclerosis, spinal cord injury, or other types of chronic voiding dysfunction. (See policy description of sacral nerve neuromodulation/stimulation coverage provided by Blue Cross Blue Shield available online at: http://www.bcbsms.com/com/bcbsms/apps/PolicySearch/views/ViewPolicy.php?&noprint=yes&path=%2Fpolicy%2Femed%2FSacral_Nerve_Stimulation.html)

In another conventional approach, a similar method is used in peripheral neurostimulation (PNS) treatment systems. Generally, candidates for peripheral neurostimulation are assessed to determine their suitability for undergoing the PNS procedure. Prior to the surgery, the patient will undergo pre-surgical testing that includes routine blood tests as well as neuropsychological evaluation. The PNS procedure itself is typically performed in two separate stages. Each stage takes about one hour, and the patient can go home the same day.

In this aspect, Stage 1 involves implanting of trial electrodes, via small needles, which are connected to an external pulse generator (EPG), typically worn on a belt of the patient. A number of stimulation programs are administered over the next few days. If this trial demonstrates a significant improvement in the patient's headache or facial pain, permanent implantation can take place. In Stage 2, a new set of electrodes, the width of angel-hair pasta, are implanted under the skin. These are connected to a smaller implantable pulse generator implanted under the skin in the chest, abdomen, or back.

Among the drawbacks associated with these conventional approaches, is the discomfort associated with wearing an EPG. The effectiveness of a trial period such as in PNE and Stage 1 trial periods are not always indicative of effective treatment with a permanent implanted system. In one aspect, since effectiveness of treatment in a trial period may rely, in part, on a patient's subjective experience, it is desirable if the discomfort and inconvenience of wearing an EPG by the patient can be minimized so that the patient can resume ordinary daily activities without constant awareness of the presence of the EPG and treatment system. This aspect can be of particular importance in treatment of overactive bladder and erectile dysfunction, where a patient's awareness of the device could interfere with the patient's experience of symptoms associated with these conditions.

In one aspect, the invention allows for improved assessment of efficacy during trial periods by providing a trial system having improved patient comfort so that patients can more easily recognize the benefits and effectiveness of treatment. In another aspect, the portions of the EPG delivering the therapy are substantially the same as the IPG in the permanent system such that the effects in permanent treatment should be more consistent with those seen in the trial system.

In certain embodiments, the invention provides an EPG patch worn on a skin of the patient so as to improve patient comfort. Optionally, the EPG used in Stage 1 may be smaller than the IPG used in the corresponding Stage 2 so that the EPG can easily be supported by and sealed against contamination by an adherent patch that covers the EPG. In one aspect, the EPG is a modified version of the implantable IPG used in Stage 2. The IPG may be modified by removal of one or more components, such as removal of a remote charging coil with a smaller battery and associated components. In addition, the EPG may use a thinner, lighter housing than the IPG, since the EPG is not required to last for many years, such as the IPG would be. The EPG therefore, may be configured to be disposable. These aspects allow the EPG to be supported within a patch adhered to the skin of the patient at a convenient and comfortable location.

FIG. 1 illustrates an example trial neurostimulation system 100 having an EPG patch 10. As shown, the neurostimulation system is adapted to stimulate a sacral nerve root. The neurostimulation system 100 includes an EPG 40 attached to the lower back region, from which a neurostimulation lead 60 extends through a foramen of the sacrum to electrodes (not shown) disposed near the sacral root. The neurostimulation lead 60 further includes an anchor (not shown) disposed on a dorsal side of the sacrum. It is appreciated, however, that the anchor may be disposed on a ventral side of the sacrum as well, or within the foramen itself. In one aspect, the EPG 40 is disposable and discarded after the trial is complete. Typically, the trial may last anywhere from 4 days to 8 weeks. Typically, an initial assessment may be obtained after 4-7 days and, if needed, effectiveness of treatment may be examined after a few weeks, typically about 2 weeks. In one aspect, the EPG 40 of the EPG patch 10 is of a substantially similar design as the IPG that would be implanted if the trial proves successful, however, one or more components may be removed to allow the EPG to be smaller in size, lower in mass, and/or differing materials are used since the device may be intended for one time use. It is appreciated that the EPG 40 could be supported during the trial by various other approaches, such by use of surgical tape, a belt or holster.

Figure 2A:
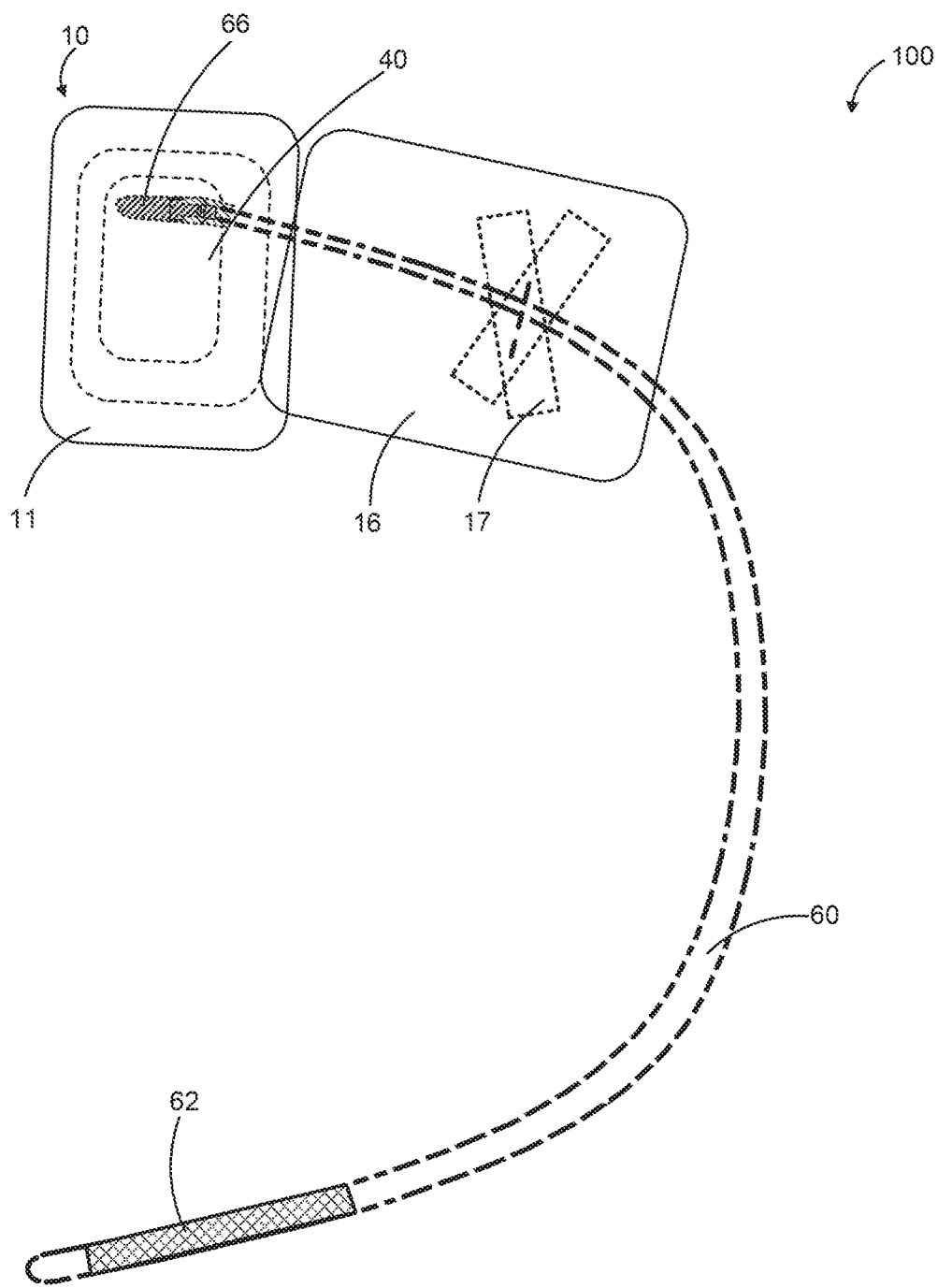
FIG. 2A shows an example neurostimulation system for a percutaneous nerve evaluation with a single electrode coiled lead.

FIG. 2A shows an embodiment of neurostimulation system 100, similar to that in FIG. 1, in more detail. As can be seen, the neurostimulation lead 60 includes a neurostimulation electrode 62 at a distal end configured for PNE use and is electrically connected to EPG 40 by a proximal contact connector 66, typically through trial cable. The EPG 40 is supported within an adherent patch 11 when attached to a skin of the patient. Optionally, another adherent patch 16 and surgical tape 17 can be used to cover the incision where the lead or cable exits the patient's body. The features of the proximal contact connector 66 are described in further detail in FIGS. 8A-10B.

Figure 2B:
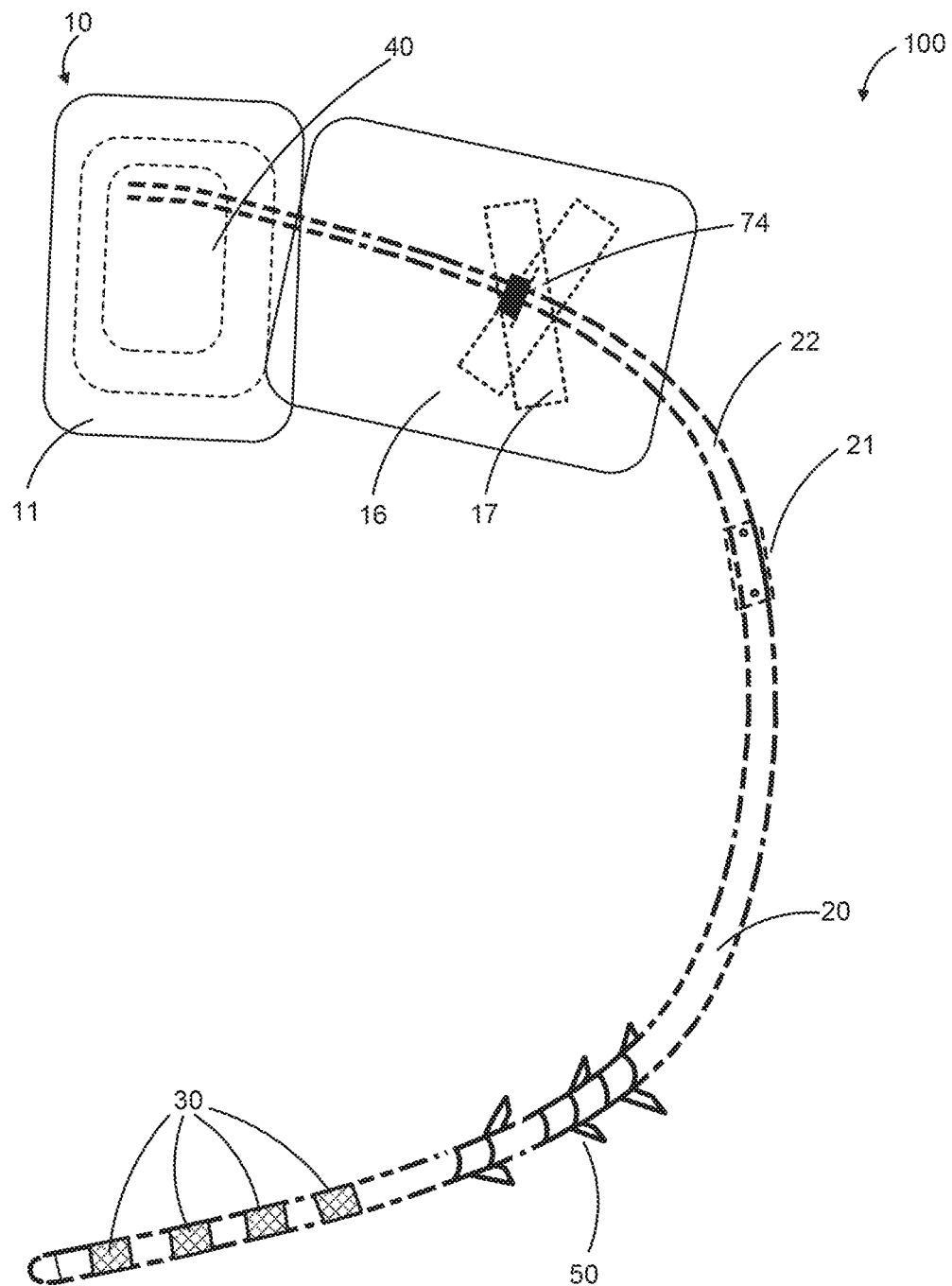
FIG. 2B shows an example neurostimulation system for a trial period with a fully implanted tined lead and lead extension.

FIG. 2B illustrates an alternate embodiment of neurostimulation system 100, similar to that in FIG. 1, in more detail. System 100 includes a tined neurostimulation lead 20 attached to EPG 40 via lead extension cable 22 at connector 21. Lead extension cable 22 includes a regression stopper 74. As can be seen, the neurostimulation lead 20 includes a plurality of neurostimulation electrodes 30 at a distal end of the lead and an anchor 50 having a plurality of tines disposed just proximal of the electrodes 30. Regression stopper 74 inhibits movement of the lead into the patient's body at the secondary incision site. The tined anchors are disposed near and proximal of the plurality of electrodes so as to provide anchoring of the lead relatively close to the electrodes. The EPG 40 is supported within an adherent patch 11 when attached to a skin of the patient. Optionally, another adherent patch 16 and surgical tape 17 can be used to cover the incision where the lead or cable exits the patient's body. Examples of regression stoppers and lead extensions are detailed further in FIGS. 3B, 3C and 11-13B.

Figure 3:
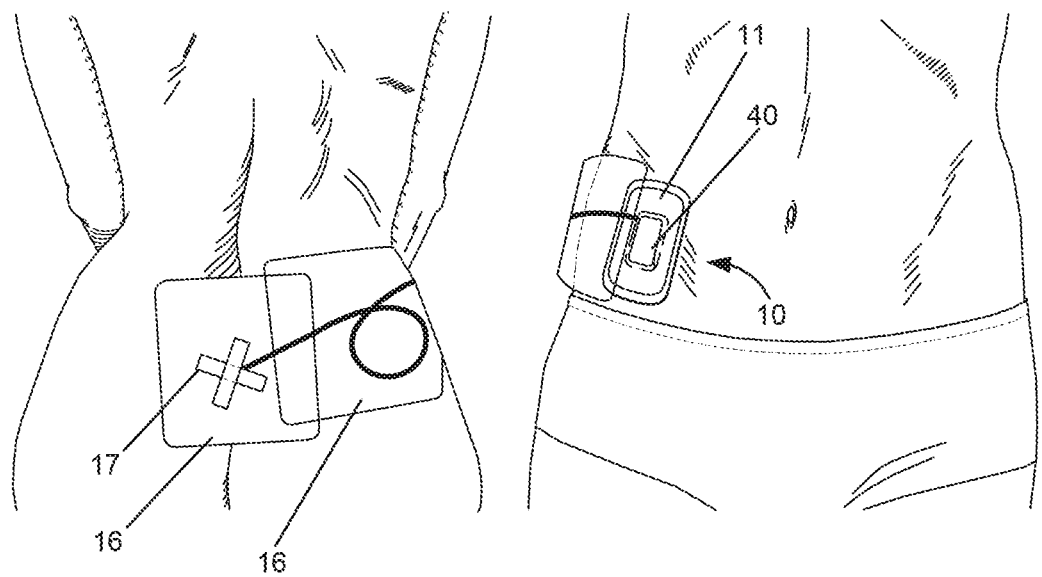
FIG. 3 is an example configuration of a trial neurostimulation system, in accordance with some embodiments.

FIG. 3 illustrates an alternate configuration in which the lead is sufficiently long to allow the EPG patch 10 to be placed to allow the patient more mobility and freedom to resume daily activities that does not interfere with sitting or sleeping. Excess lead can be secured by an additional adherent patch 16 and surgical tape 17, as shown by the center patch in FIG. 3A. In one aspect, the lead is hardwired to the EPG, while in another the lead is removable connected to the EPG through a port or aperture in the top surface of the flexible patch 11. In one aspect, the EPG patch and extension cable are disposable such that the implanted lead can be disconnected and used in a permanently implanted system without removing the distal end of the lead from the target location. In another aspect, the entire trial system can be disposable and replaced with a permanent lead and IPG. In one aspect, the EPG unit may be wirelessly controlled by a patient remote in a similar or identical manner as the IPG of a permanently implanted system would be. The physician may alter treatment provided by the EPG through use of a portable clinician unit and the treatments delivered are recorded on a memory of the device for use in determining a treatment suitable for use in a permanently implanted system. Such systems can include a trial PNE lead such as that shown in FIGS. 8A-8B.

Figure 4:
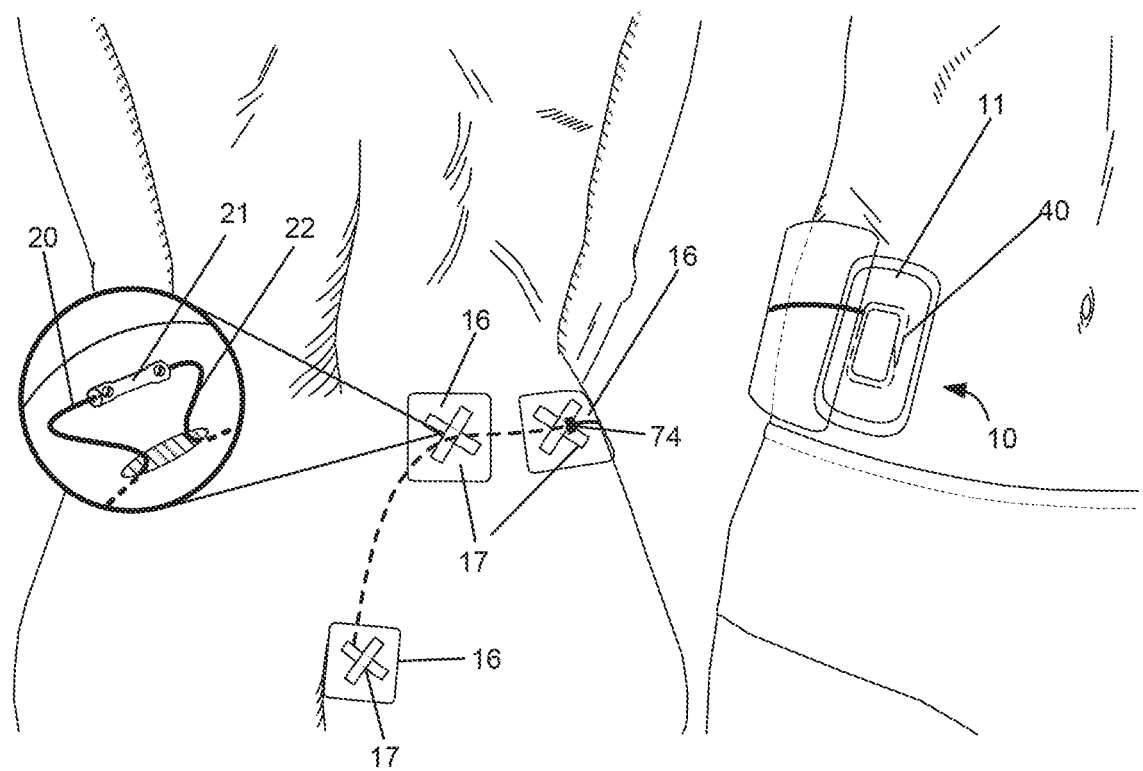
FIG. 4 is yet another alternative configuration of a trial neurostimulation system, in accordance with some embodiments.

FIG. 4 illustrates an alternate configuration in which a tined neurostimulation lead 20 is connected through a connector 21 at a first incision site, via a lead extension that is tunneled to a secondary incision site where it exits the body. This allows for the implanted lead to be used for both the trial and permanent system. This also allows the lead 20 of a length suitable for implantation in a permanent system to be used. Three access locations are shown: two percutaneous puncture sites, one for the lead implantation over the sacral area, and one for the extension exit site, while in between the puncture locations an incision (>1 cm) is made for the site of the connection of the lead 20 and the extension cable 22. Lead extension 22 includes regression stopper 74 that is positioned outside the body so as to engage an outer skin of the patient and inhibit subsequent regression of the lead into the patient's body during the trial or during explant. This approach minimized movement of the implanted lead 20 during conversion of the trial system to a permanently implanted system. During conversion, the lead extension 22 can be removed along with the connector 21 and the implanted lead 20 attached to an IPG that is placed permanently implanted in a location at or near the site of the first percutaneous incision. In one aspect, the connector 21 may include a connector similar in design to the connector on the IPG. This allows the proximal end of the lead 20 to be coupled to the lead extension 22 through the connector 21 and easily detached and coupled to the IPG during conversion to a permanently implanted system.

Figure 5:
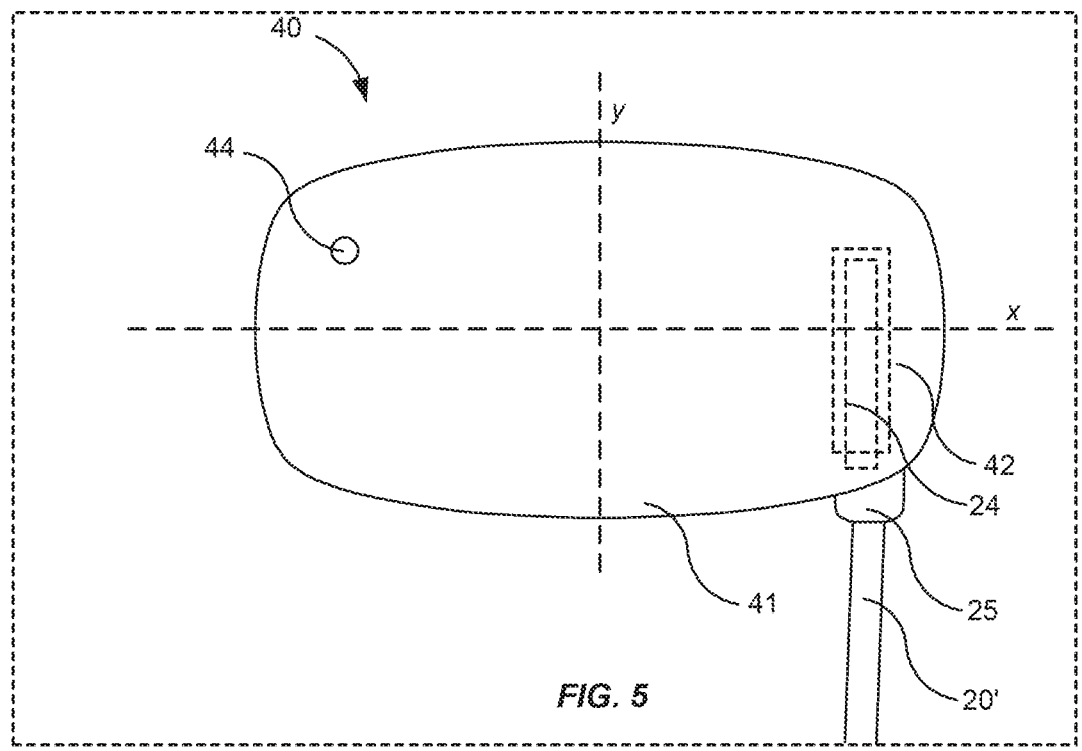
FIG. 5 illustrates an EPG and an associated schematic in accordance with some embodiments.

FIG. 5 illustrates an example EPG 40 for use in a neurostimulation trial in accordance with various aspects of the invention. EPG 40 includes a substantially rigid outer shell or housing 41, in which is encased a stimulation pulse generator, a battery and associated circuitry. EPG 40 also includes a connector receptacle 42 accessed through an opening or port in the outer housing 41 and adapted to electrically connect with a proximal lead connector 24 of a neurostimulation lead 20'. Although EPG 40 is shown connected with neurostimulation lead 20', lead 20, cables 22 may also be connected to EPG 40. Connector receptacle 42 includes multiple electrical contacts (e.g. six contact pins, eight-contacts pins), all or some of which can be connected to corresponding contacts points on a connector coupled thereto, depending on the type of connector. Connector receptacle 42 could be configured according to varying types of connector standards beyond that shown, for example, a USB or lightning cable connector. Lead connector 24 can include a proximal plug or boot 25 that sealingly engages the port when lead connector 24 is matingly connected within connector receptacle 42 to further secure the mated connectors and seal the port from intrusion of water, humidity or debris. Boot 25 can be formed of a pliable material, such as an elastomeric polymer material, that is fittingly received within the port so as to provide ingress protection. In some embodiments, this configuration provides an ingress protection rating (IPR) is provided at IP24 or better. In this embodiment, connector receptacle 42 includes multiple electrical contacts, each operatively coupled with the stimulation pulse generator, so that the EPG can deliver neurostimulation pulses to multiple neurostimulation electrodes of the lead when coupled to the connector receptacle 42.

In one aspect, EPG 40 is configured with a multi-purpose connector receptacle 24. For example, connector receptacle 42 can be coupled with either a neurostimulation lead 20' as described above, or can be coupled with a power connector of a charging cord to allow recharging of an internal battery of EPG 40. Such a configuration is advantageous as it allows the EPG housing 41 to be designed with a single opening or access port, which further reduces the potential exposure of internal components to water and debris, since the port is sealingly occupied by the lead connector during delivery of therapy during the trial period. In contrast, a device having a separate charging port would likely either remain open or may require use of a removable plug or cover to seal the additional port.

In another aspect, EPG 40 is designed as a substantially planar polygonal prism having parallel major surfaces that are positioned flat against the patient's body when affixed to the patient during the trial period, such as the rectangular prism shown in FIG. 5.

Figure 6:
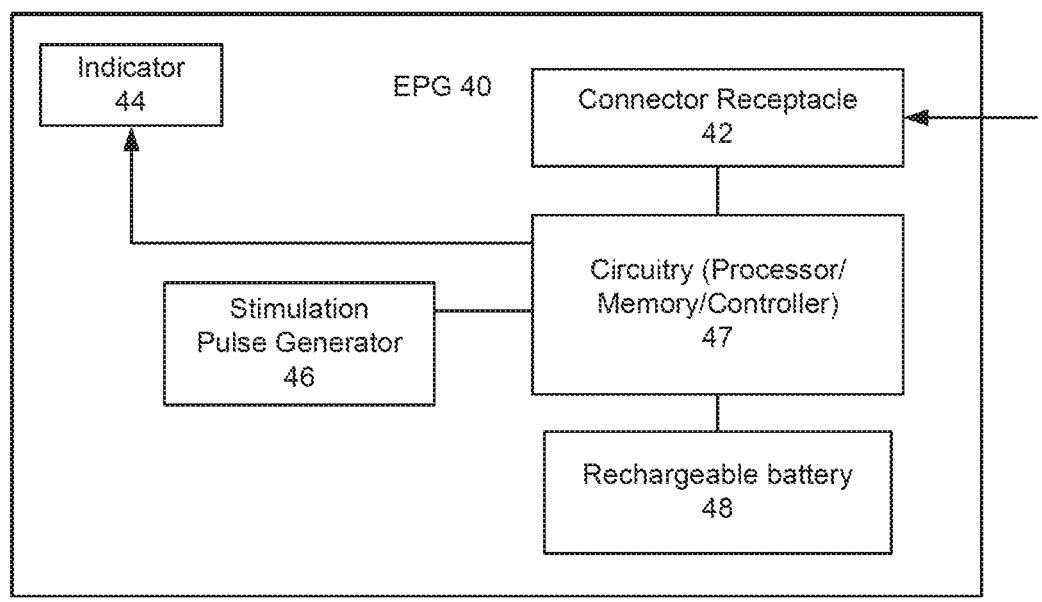
FIG. 6 shows a schematic of an EPG in accordance with some embodiments.

FIG. 6 shows a schematic of the example EPG 40 having a multi-purpose connector receptacle 42. EPG 40 includes the stimulation pulse generator 46 and rechargeable battery 48 each coupled to connector receptacle 42 via associated circuitry 47 that controls delivery of power to and from the rechargeable battery 48 and the stimulation pulse generator 46 and connector receptacle 42. Circuitry 47 can include one or more processors, controllers and a recordable memory having programmable instructions recorded thereon to effect control of the stimulation pulse generation, rechargeable battery discharge and charging, and indicator 44. In some embodiments, memory includes pre-programmable instructions configured to effect multiple different operating modes, for example the therapy mode and charging mode. In the therapy mode, circuitry 47 uses the rechargeable battery 48 to power the stimulation pulse generator 46, which produces stimulation pulses that are delivered to a connected neurostimulation lead via the connector receptacle 42. In the charging mode, circuitry 47 controls delivery of power delivered via the connector receptacle 42 to rechargeable battery 48. In some embodiments, circuitry 47 includes a controller that switches between differing modes, which can be effected upon connection of a certain connector types into connector receptacle 42. For example, in some embodiments, EPG 40 can include a detector that can detects a certain type of connector (e.g. lead connector, charging connector). In other embodiments, a connector type can be determined by measurement or detection of electrical characteristics of the connection. For example, a charging connection may require electrically connectivity with only a certain number of electrical contacts (e.g. one, two, etc.) and a ground, while a neurostimulation lead may connect with all of the designated electrical contacts without any grounding required. In some embodiments, the mode can be set be manually or wirelessly set by a user as needed.

In another aspect, trial neurostimulation system 100 includes an affixation device that secures EPG 40 to the patient while connected to a neurostimulation lead implanted at a target tissue within the patient. Typically, the affixation device is configured to secure the EPG on a mid-portion (e.g. lower back region) or hip of the patient, either through an adherent patch applied directly to a skin of the patient or a clip device that can be releasably attached to a garment of the patient. Various examples of differing types of affixation devices are described herein.

Figure 7A:
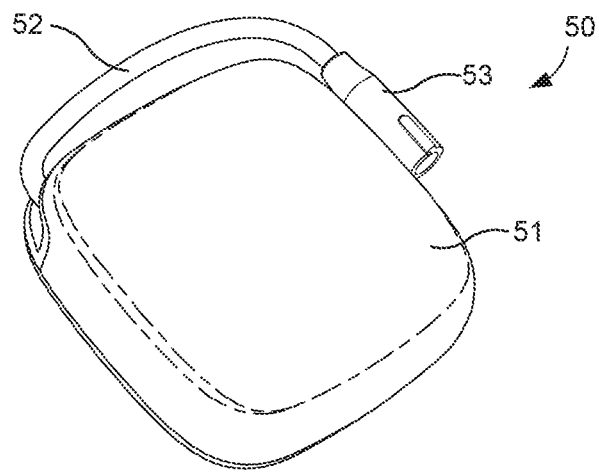
FIGS. 7A-7B illustrate an alternative EPG in accordance with some embodiments.
Figure 7B:
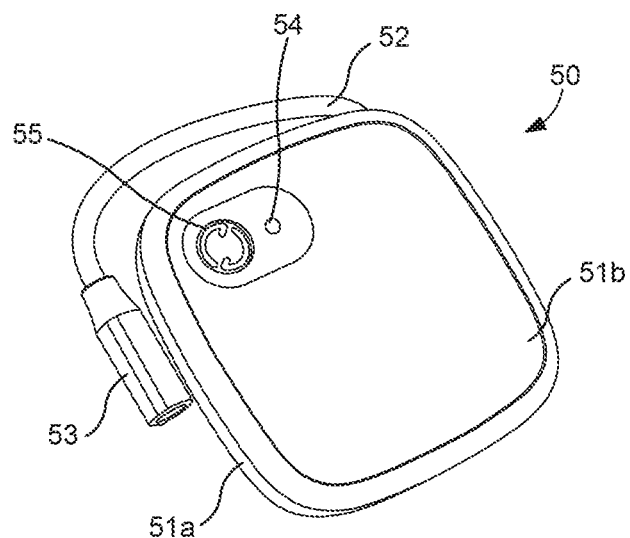

FIGS. 7A-7B illustrate an alternative EPG 50 that includes a housing 51 from which a short cable connector 52 extends to a lead connector 53. In this embodiment, lead connector 53 is a multi-pin connector suitable for electrically connecting to a neurostimulation lead having multiple electrodes through an intermediate adapter or lead extension cable (see FIG. 13). Typically, cable connector 52 is relatively short, for example a length between 1 and 12 inches, preferably 3 and 6 inches. In this embodiment, the multi-pin connector is a 4-pin connector suitable for connecting to a neurostimulation lead having four electrodes, however, it is appreciated that lead connector could include differing numbers of pins so as to be suitable for connection with neurostimulation leads having greater or fewer neurostimulation electrodes. In other embodiments, the lead connector can be configured with a receptacle 42 for connecting with a proximal lead connector of a neurostimulation lead, such as described previously in other embodiments. The EPG can be used with a tined lead trial or a temporary lead (PNE lead) trial. Configuring the connection to the lead external of the housing allows the EPG to be even smaller and lighter than those with the connection integrated within the device. Such a configuration also allows for some movement for adjustment or handling of the EPG while minimizing movement of the proximal lead connector, which can be secured by tape to the patient's body just proximal of the connector.

In some embodiments, the short cable connector 52 or "pigtail connector" is integrated with the EPG such that the electrical connections between the cable and the internal electronics of the EPG are permanently attached and sealed. This allows the EPG to further withstand intrusion of fluids and moisture during the trial stimulation period.

Depending on the selection of cables desired for use, the EPG may be used with a PNE lead (which may have one or more than one electrode and conductor), or a permanent lead. In addition, the EPG may be used for bilateral stimulation (the use of two leads, one for each for a patient's left and right sides) when a bilateral connector cable is used between the EPG and leads.

In some embodiments, the EPG includes a non-rechargeable single-use power source (e.g. battery) having sufficient power for operation of the EPG for at least the duration of the trial period (e.g. days, weeks, months). In such embodiments, the power source can be integrated and non-removable or non-replaceable by the patient.

As can be seen in FIG. 7B, EPG housing 51 can be defined as two interfacing shells, top shell 51a defining the outer major surface and a majority of the side surfaces and bottom shell 51b defining an underside surface. In this embodiment, EPG has a substantially rectangular (e.g. square) prism with rounded edges. The top major surface can be shaped with a slightly convex contour, while the underside includes a substantially flattened surface for placement against the patient. Typically, the interfacing shells 51a, 52b are formed of a rigid or semi-rigid material, such as hardened polymer, so as to protect and seal the electronics within.

In some embodiments, the EPG includes one or more user interface features. Such user interface features can include any of a button, switch, light, touch screen, or an audio or haptic feature. In the embodiment shown in FIGS. 7A-7B, EPG 50 includes a button 55 and an LED indicator 54. Button 55 is configured to turn EPG 50 on from an off or hibernation state. When turned on, EPG can communicate with an external device, such as a clinician programmer to receive programming instructions, and can deliver stimulation to a connected neurostimulation lead while in an operating state. While button 55 can be used by the patient to turn EPG 50 on, it is appreciated that this functionality can be concurrent with any other functionality described herein. For example, EPG 50 can be further configured to be turned on from an off or hibernation state by use of a patient remote or can be configured to suspend delivery of stimulation upon detachment of the neurostimulation lead. It is appreciated that while a button is described in this embodiment, any actuatable user interface feature could be used (e.g. switch, toggle, touch sensor) that is typically actuatable between at least two states.

In this embodiment, EPG 50 is configured such that pressing button 55 turns on a communication function of the EPG. Once actuated, the EPG has a pre-determined period of time (e.g. 60 seconds, 90 seconds) to wirelessly connect to an external programmer (e.g. Clinican Programmer). If the EPG connects to the clinician programmer, the EPG stays on to facilitate programming and operating to deliver of stimulation per programming instructions. If connection is not successful, the EPG automatically turns of. If button 55 is pressed when EPG is on, nothing happens and the communication or operating remains unchanged. If a patient desires to turn off stimulation, the patient remote could be used or alternatively, detachment of the neurostimulation lead could also suspend stimulation. Since subsequent pressing of button 55 during operation does not turn the EPG to the off or hibernation state, the button can be positioned on an underside of the EPG that is placed against the patient when worn during the trial stimulation period, although it is appreciated that the button could be disposed anywhere on the housing of the EPG. Thus, in this embodiment, the functionality of button 55 facilitates initial programming during set-up of the trial period or for reprogramming, but does not require interaction by the patient during the trial period. Typically, control or adjustment of stimulation by the patient would be performed by use of the patient remote. In some embodiments, the EPG is provided in a hibernation mode and communication can be initiated by actuation of a button on the EPG to facilitate programming with the CP. In some embodiments, when the patient remote is used to turn stimulation off, the EPG returns to the hibernation state and only the CP can fully turn the EPG to an off-state. In some embodiments, the EPG includes a single button thereon configured as described in any of the embodiments herein.

Figure 8A:
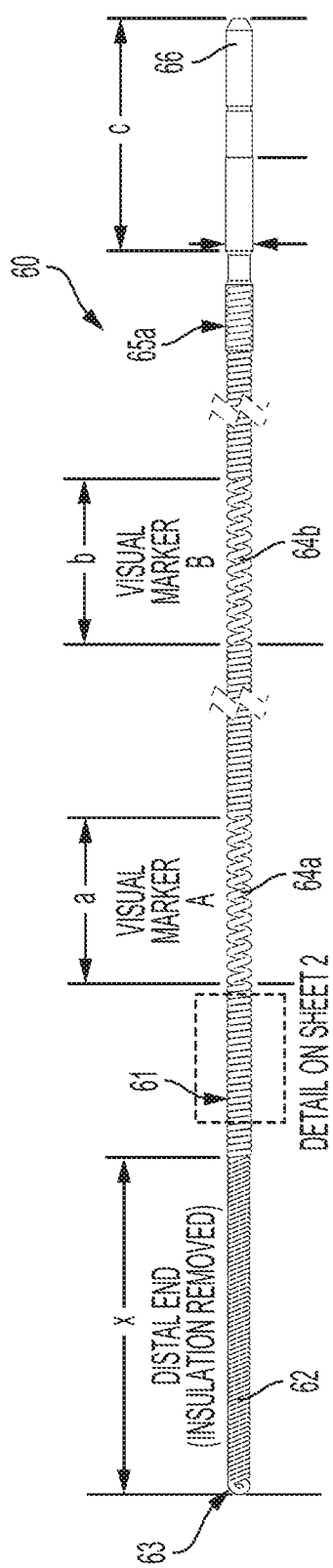
FIGS. 8A-8B illustrate a neurostimulation lead configured for a percutaneous nerve evaluation or trial period, in accordance with some embodiments.
Figure 8B:
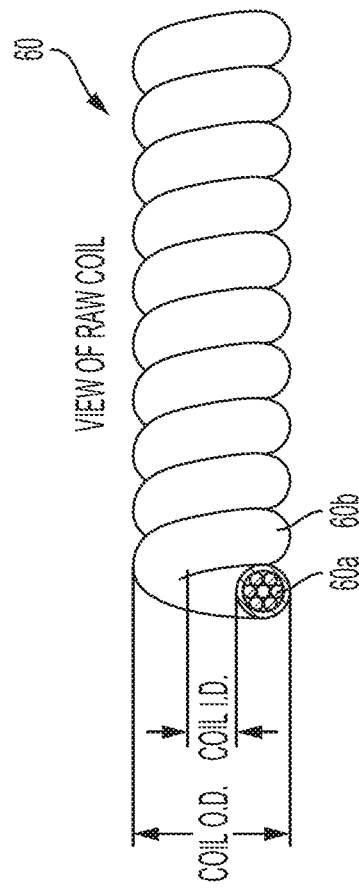

FIGS. 8A-8B depict an exemplary neurostimulation lead configured for use a temporary lead for use in a trial, such as a PNE. FIGS. 9A-10B illustrate features of a proximal connector of the lead that facilitate improved retention of the lead during the trial period. It is appreciated that any of the features described herein pertaining to the temporary lead are applicable to any neurostimulation lead, including fully implanted leads for use in a long-term or permanently implanted neurostimulation system.

As shown in FIG. 8A, the neurostimulation lead is defined by a coiled conductor 61 having an insulted coating along its length and a distal electrode portion 62 defined by an exposed portion of the coiled conductor without the insulting coating. The distal end of the electrode 62 includes an atraumatic tip 63 to avoid damage to tissues. In some embodiments, the atraumatic tip is formed by melting the distal tip of the exposed coiled conductor, for example by heating or welding, so as to form a ball-shaped tip. In some embodiments, the heat affected tip extends no more than 0.03" from tip. The coiled lead can include one or more markers 64a, 64b along an intermediate portion of the lead to facilitate positioning and implantation of the lead at a targeted tissue. In this embodiment, the markers are defined by an open coil portion, the remainder of the lead being closed wound. In other embodiments, the markers portions are stretched to form the open coil portion. In some embodiments, the lead is wound so as to form the open coiled portions defining the markers and the closed wound portions. This latter approach is advantageous over stretching portions as it avoids plastic deformation of the conductor and associated stresses on the conductor along the open coil portions. It is appreciated that the markers can be defined by various other features, for example visible markings, such as coating, applied onto the coiled conductor.

In one aspect, the dimensions of the lead are defined in accordance with a given application of the neurostimulation lead. The embodiment depicted in FIG. 8A is configured for use as a PNE lead for sacral nerve modulation, the single electrode being inserted through a foramen needle inserted through a sacral foramen and positioned adjacent a sacral nerve root. A sufficient length of the lead remains outside the patient for attachment to an external pulse generator, either directly or through an intermediate cable, for a nerve stimulation evaluation or trial. For such an application, the overall length of the lead can be between 12" to 24", typically about 16". The length of the distal electrode can be within a range of 0.1" to 1", typically about 0.2" to 0.6", preferably about 0.4". In some embodiments, the exposed surface area of the distal electrode is within a range of 0.01 $in^2$ to 0.1 $in^2$, typically between 0.02 $in^2$ and 0.05 $in^2$, preferably about 0.027 $in^2$. In some embodiments, the length and/or surface area of the lead corresponds to a lead of the permanently implanted neurostimulation lead.

Typically, the outer diameter of the lead is about 0.025" to facilitate passage through a foramen needle. The lead includes two markers, visual marker A (64A) and visual marker B (64B), positioned at two different locations corresponding to two differing lengths of respective foramen needles. Visual marker A is positioned at a first distance (e.g. 4-5") from a distal end of the lead for use with a first foramen needle of a corresponding length and visual marker B is positioned at a second distance (e.g. about 6-7") from a distal end of the lead for use with a second foramen needle of corresponding length. The differing lengths correspond to different locations at which the target region is located as suited for a particular patient or application. The open coiled markers can be between 0.1" to 0.5", or any suitable length. In the closed wound portions, the pitch (taken as an average measurement over 10 turns) is between 0.005 to 0.05", typically about 0.010". In the open coil portions, the pitch is within a range of about 0.01 to 0.05", typically about 0.03". In this embodiment, each open coiled marker is about 0.2" in length. It is appreciated that such a lead could include a single marker, two markers, or multiple markers corresponding to differing locations as need for a given application.

As shown in FIG. 8B, the conductor can be comprised of a multi-filar conductor 60a having an outer insulative coating 60b. In this embodiment, the conductor 60a is a 7-strand wire of stainless steel (e.g., 316 SS) and the insulating coating thickness is between 0.0005" and 0.005". The inner diameter can be within a range of 0.001 to 0.01". The outer diameter can be within a range of 0.01 to 0.05". It is appreciated that the above dimensions of the lead are suited for the particular application of sacral neuromodulation described herein, and that various other dimensions could be utilized as needed for a given type of stimulation (e.g. spinal neuromodulation, deep brain stimulation).

In another aspect, a proximal end of the lead 60 is coupled to a proximal contact connector 66, the conductor being electrically coupled and fixedly attached to the proximal contact connector. In some embodiments, the proximal connector 66 is dimensioned for passage through the foramen needle, for example, in the application described above, the proximal connector has an outer diameter of about 0.025". An outer cover 65a (e.g. shrink tubing) is applied over the interface between the coiled conductor and the proximal connector 66. FIGS. 9A-10B show various detail views of the proximal contact connector 66 (shown before attachment to the coiled conductor).

As can be seen in FIGS. 9A-9C, the proximal contact connector 66 includes a distal portion 66a for electrically coupling with the conductor of the coiled conductor and a proximal portion 66b for coupling with an external pulse generator or intermediary cable and facilitating handling of the lead. The distal portion 66a includes a distal end 69, a retention flange 68 and a coupling portion 67 that is proximal of the retention flange. One or more coils at the proximal end of the coiled conductor are fixedly attached (e.g. by soldering or laser welding) to coupling portion 67. The distal end 69 is sized to be fittingly received within the inner diameter of the coiled lead. The retention flange includes a distal facing ramped surface 68a that is tapered for facilitating introduction of the coiled conductor onto recessed coupling portion 67. In this embodiment, the ramped surface 68a extends only partly about the circumference of the connector and includes a notch 68b that allows introduction of a proximal end of the conductor to be fed past the flange and onto the coupling portion, for example, by screwing or gently pushing and rotating the conductor to advance one or more coils onto the coupling portion 67. The retention flange 68 further includes a proximal facing retention surface 68c that is substantially perpendicular to the longitudinal axis of the lead and connector so as to retain the coiled conductor by engagement with a coil of the coiled conductor on the coupling portion.

Engagement of one or more coils of the coiled conductor against the proximal facing retention surface resists the load from tension on the coiled lead and removes the load and stress concentration from the weld joint of the conductor along the coil portion, thereby protecting the weld joint. In this embodiment, the retention surface is configured to withstand a minimum tensile force when the coiled conductor is pulled in the distal direction. In this embodiment, the retention surface of the retention flange 68 is perpendicular to the longitudinal axis of the connector 66.

The proximal portion 66b of the connector extends a sufficient length to facilitate connection of the proximal contact connector to a pulse generator or intermediary cable. The proximal portion has a length, l, between 0.1" and 0.5", typically about 0.25" and can include an indented feature, 65b, to be used as a visual indicator for alignment of the cover (e.g. shrink tube) formed of any suitable material (e.g., polymer, PET). The indented portion can be spaced a distance $l_1$ away from the proximal end of the connector, typically between 0.1 to 0.2". The proximal end 66c includes an opening through which a style can be inserted through the proximal contact connector 66 and through the lead to the distal end to stiffen the lead and facilitate insertion of the lead through the foramen needle. After placement of the distal electrode at the target electrode, the foramen needle can be removed and the stylet withdrawn. In this embodiment, the proximal end of the contact connector 66 is tapered at angle a1, which can be between 30-60 degrees, typically about 40 degrees. The outside diameter of the proximal contact connector is substantially the same as that of the lead to facilitate passage through a foramen needle. In this embodiment, the outside diameter is about 0.023".

Figure 10B:
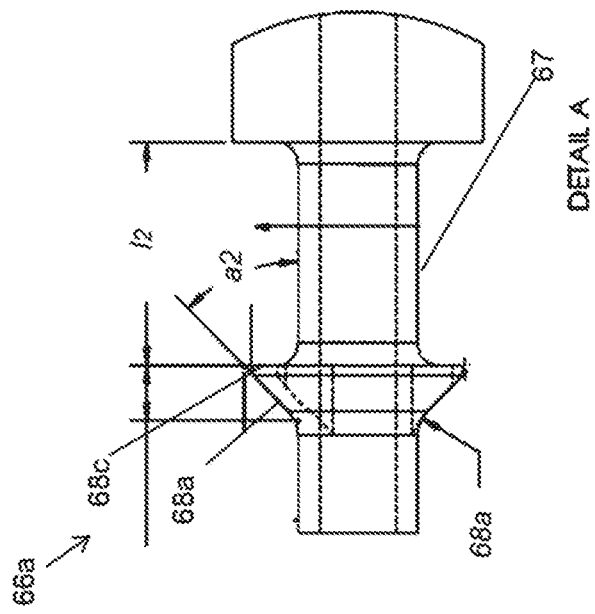
FIGS. 10A-10B illustrate front and side views, respectively, of a distal portion of the proximal contact connector, in accordance with some embodiments.
Figure 10A:
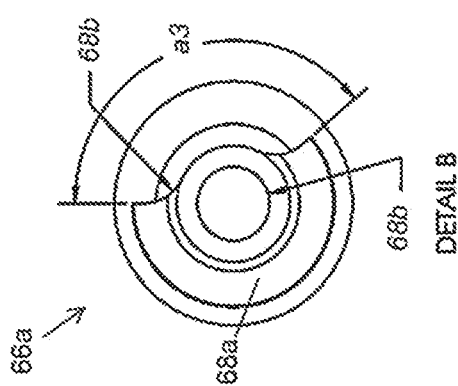

FIGS. 10A-10B illustrate further details of the distal portion 66a of the proximal contact connector 66. As shown, the retention surface has a width of 0.005" extending circumferentially about at least part of the coupling portion. In some embodiments, the retention surface is substantially perpendicular (90 degree+/−10 degrees). It is appreciated that the stop feature could be slightly angled and still withstand a desired minimal tensile force. In this embodiment, the retention feature is configured to withstand a minimum tensile force, for example at least 5 N, preferably at least 10-12 N. It is appreciated that this minimum tensile force can differ according to the mechanical properties of the conductor/lead configuration, as well as the region in which the lead is implanted. The distal facing ramp surface 68a can be distally tapered at an angle, a2, from the longitudinal axis. In some embodiments, the angle a2 is between 30 to 60 degrees, in the embodiment shown, this feature is about 45 degrees. The ramp surface can extend a suitable distance, for example, between 0.002" and 0.01". The notch 68b can extend along an angled, a3, about the circumference, for example between 90 to 180 degrees. In this embodiment, angle a3 is about 140 degrees about the circumference. The recessed coupling portion 67 extends a sufficient distance for one or more coils to be positioned along the portion and electrically coupled and fixedly attached thereto, such as by bonding, soldering or laser welding. In some embodiments, the coupling portion extends between 0.01 to 0.05". In this embodiment, the coupling portion 67 extends about 0.02". While the above dimensions provide retention to withstand a minimum desired tensile force for the conductor coil configuration described above, it is appreciated that these dimensions can be modified as needed to provide a different desired retention force as appropriate for a given conductor or lead configuration or application.

In another aspect, a trial system can utilize a tined neurostimulation lead, similar or identical to the design of a permanently implanted tined lead, that is electrically coupled to an external pulse generator by a lead extension cable. Such tined neurostimulation leads typically include multiple electrodes and often utilize proximal connectors that mimic the connector receptacle of an IPG. Such connector receptacles are relatively larger than the proximal contact connector of the PNE lead described above. Such trial systems can be utilized for weeks or months to assess the efficacy of neurostimulation programs applied by an implanted multi-electrode neurostimulation lead. As describe above in the trial system of FIG. 4, the proximal connector of the lead is implanted within the body through a first incision area (typically at a location at which the implanted pulse generator may later be implanted) and coupled to the lead extension cable which is tunneled to exit the body at a second incision for electrically coupling to the external pulse generator. This approach avoids potential infection of the first incision area since the incision area through which the cable extends in a partially implanted system has a higher risk of infection. The movement of the extension cable during the trial period along where it exits the body can introduce contaminants or bacteria leading to an infection. Another challenge associated with the lead extension cable is regression of the distal connector through the second incision during removal of the lead extension cable and conversion of the system to a fully implanted system. To avoid these challenges associated with use of lead extension cables, the extension cable can include a lead regression stopper adapted to engage an outer surface of the skin (or a bandage or gauze placed thereon) so as to prevent regression of the lead extension into the patient's body during the trial period or during removal of the lead extension during conversion to a permanently implanted system. The stopper is dimensioned with a distal facing surface to engage an outer skin of the patient (or associated gauze), yet still sufficiently small to allow passage of the entire stopper through a cannula or delivery sheath tunneled from the first incision and through the second incision.

Figure 13A:
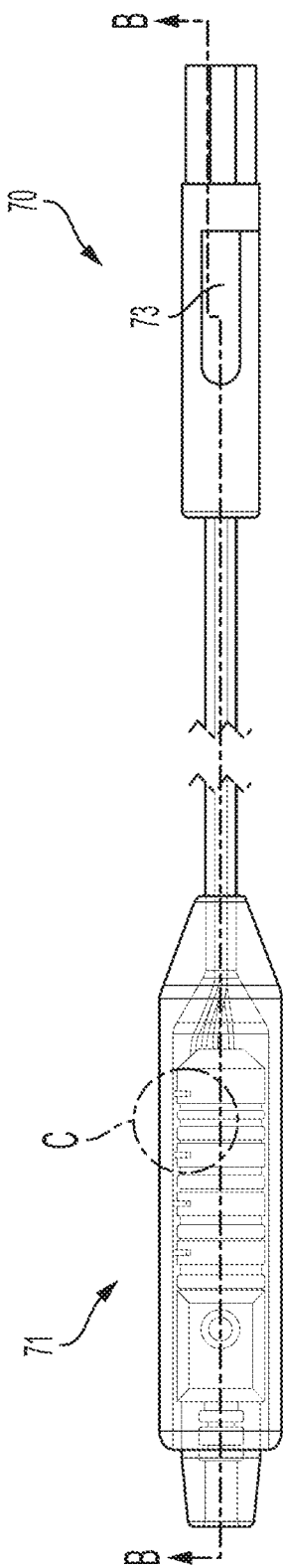
Figure 13A:
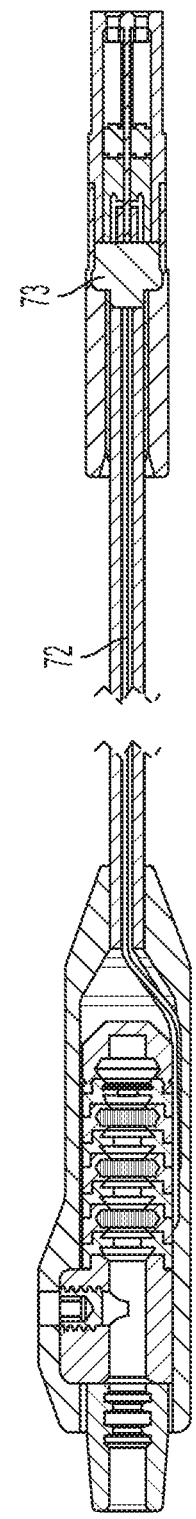

FIG. 11 shows an example lead extension cable 70 having a distal connector 71 for coupling to the implanted tined lead, a proximal connector 73 adapted for coupling with the EPG (or an intermediate connector cable/adapter) and a lead extension cable 72 electrically coupling the proximal and distal connectors. The distal connector 71 includes contacts D1, D2, D2, D3 of a canted coil spring design (e.g. Bal-seal contacts) that mimics the connector receptacle of an IPG that are electrically coupled to four contacts P0, P1, P2, P3 of the proximal connector 73, as shown in FIG. 12B, which correspond to the four conductors of the lead extension and four-electrode tined neurostimulation lead. The distal connector 71 remains implanted within the patient's body at the first incision during the trial period, while the remainder of the lead extension cable is passed through an access route tunneled from the first incision and exits the body through a second incision. To facilitate passage through the tunneled region, the proximal connector 73 and regression stopper 74 have a reduced delivery profile that corresponds to an inside diameter of the tunneling tool, for example, 0.4" or less, or typically less than 0.2" The regression stopper 74 includes a distal facing surface 74a that engages against an outer skin of the patient (or associated bandaging or gauze) when the lead extension is pulled inward toward the body, such as by flexing of the implanted lead or during the implantation or removal procedure. For the application described herein, the overall length, L1 of the extension cable is relatively long, for example, 30-40 inches. The length, L2, between the distal connector 71 and the regression stopper 74 is about 10-20", typically about 14 inches, and the length, L3, of the proximal connector is about 0.5-1". Additional views of the lead extension 70 and internal connector components are shown in FIG. 13A and the associated cross-sectional view in FIG. 13B (the regression stopper is not shown).

As shown, the regression stopper 74 is substantially cylindrical in shape, however, it is appreciated that various other shapes and designs could be utilized in accordance with the concepts described above. In some embodiments, the regression stopper 74 can include a feature for coupling to a removable stopper feature, for example, a stopper component having a further enlarged diameter. The regression stopper can be formed of a polymer, metal, or any suitable material. Typically, the regression stopper is relatively rigid, however, the stopper can be semi-rigid or malleable for patient comfort.

Figure 14A:
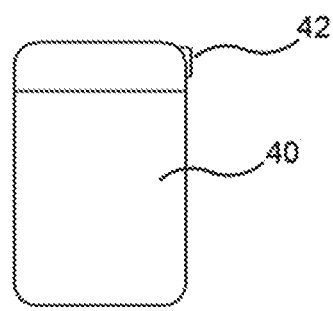
FIGS. 14A-14B illustrate an example EPG and lead extension and tine lead in accordance with some embodiments.
Figure 14B:
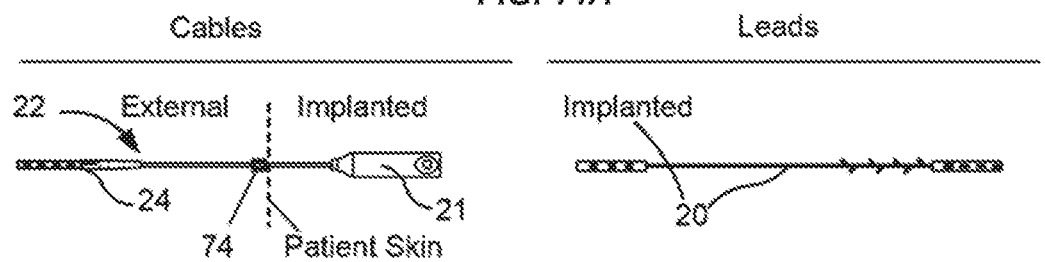

FIGS. 14A-14B show an example trial system 100 utilizing such a lead connector 22 having a regression stopper 74.

FIG. 14B depicts a lead extension 22, which includes a proximal lead connector 24 similar or identical to that on the implantable neurostimulation lead 20 and an implantable lead connector receptacle 21, which can be connected to a proximal lead connector 24 of a fully implanted neurostimulation lead 20 and a regression stopper 74 as described above. The proximal connector 24 is configured for attachment to the EPG 40 via connector receptacle 42.

Figure 15:
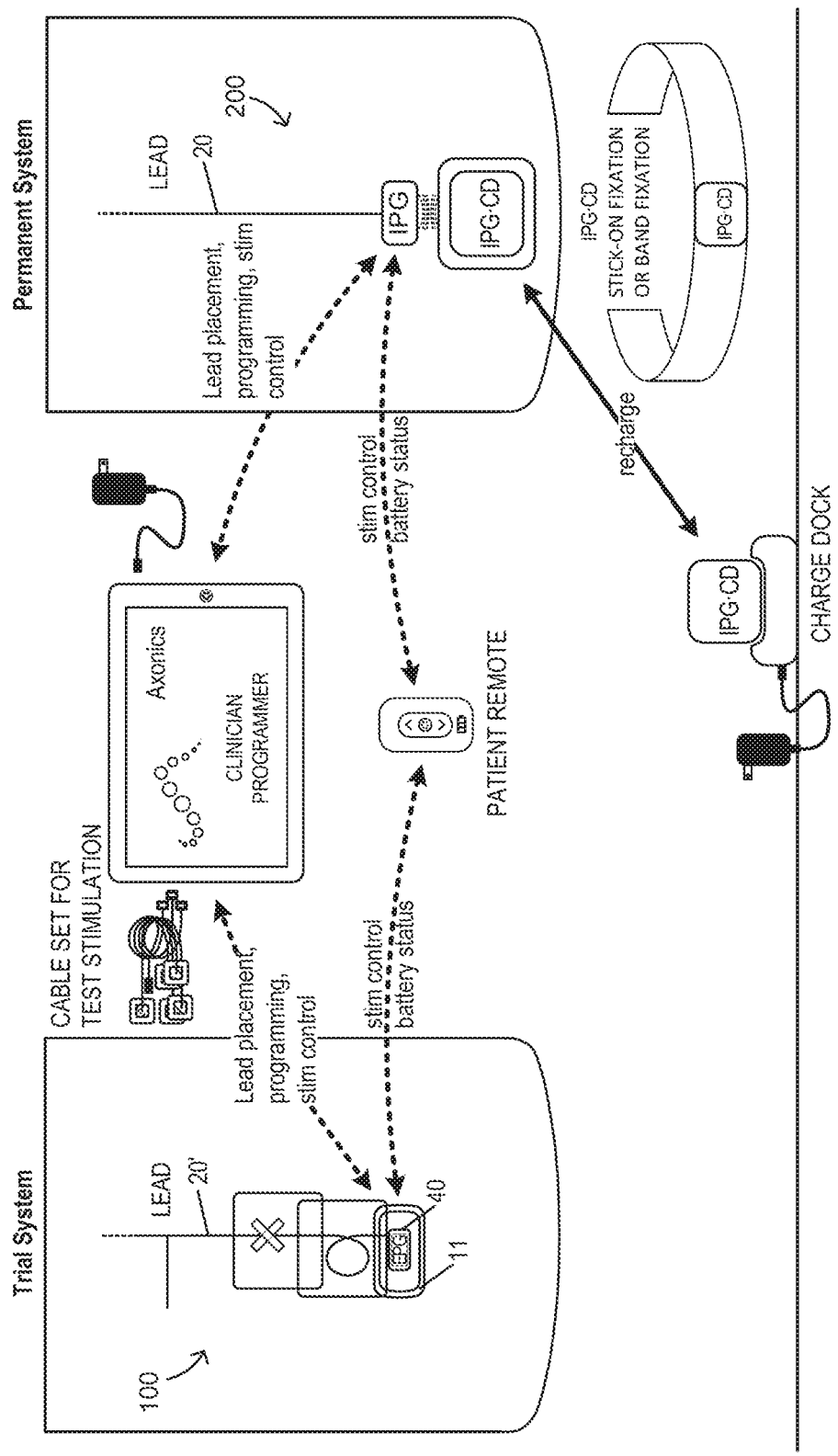
FIG. 15 schematically illustrates a use of a trial neurostimulation system utilizing an EPG affixation device in accordance with some embodiments.

FIG. 15 illustrates a schematic of a trial system 100, in accordance with aspect of the invention, and a permanent system 200 to further demonstrate the applicable uses of any of the neurostimulation leads described herein. As can be seen, each of the trial and permanent system are compatible for use with a wireless clinician programmer and a patient remote. The communication unit by which EPG wirelessly communicates with the clinician programmer and patient remote can utilize MedRadio or Bluetooth capability, which can provide a communication range of about two meters. The clinician programmer can be used in lead placement, programming and stimulation control in each of the trial and permanent systems. In addition, each allows the patient to control stimulation or monitor battery status with the patient remote. This configuration is advantageous as it allows for an almost seamless transition between the trial system and the permanent system. From the patient's viewpoint, the systems will operate in the same manner and be controlled in the same manner, such that the patient's subjective experience in using the trial system more closely matches what would be experienced in using the permanently implanted system. Thus, this configuration reduces any uncertainties the patient may have as to how the system will operate and be controlled such that the patient will be more likely to convert a trial system to a permanent system.

Figure 16:
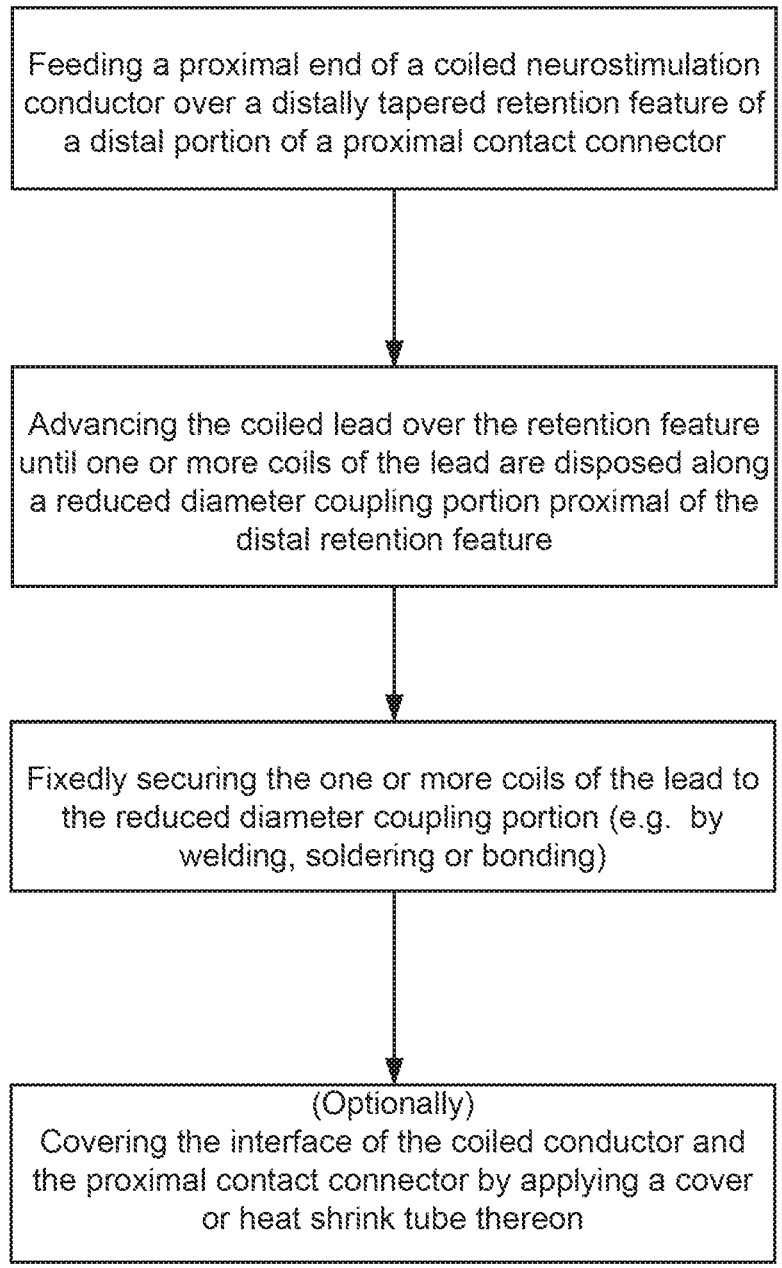
FIG. 16 illustrate a method of assembling a neurostimulation lead having a coiled conductor, in accordance with some embodiments.

FIG. 16 depicts a method of assembling a neurostimulation lead. Such a method can pertain to include assembly of trial leads, such as PNE leads, as well as leads for permanently implanted applications. Such methods can include: feeding at least one coiled conductor over a distal retention flange of a proximal contact connector so as to position one or more coils of the at least one coiled conductor along a reduced profile coupling portion of the proximal contact connector proximal of the distal retention flange and electrically coupling and fixedly attaching the coiled conductor to the coupling portion by soldering or welding. Such methods further include engaging a proximal facing surface of the distal retention flange with a portion of the one or more coils disposed proximal of the retention flange so as to withstand tensile forces applied by tension in the lead, thereby maintaining the integrity of the electrical connection between the coiled conductor and the proximal contact connector. In some embodiments, an insulative polymer cover such as shrink tube is advanced over the interface of the coiled conductor and the proximal contact connector for protection.

Figure 17:
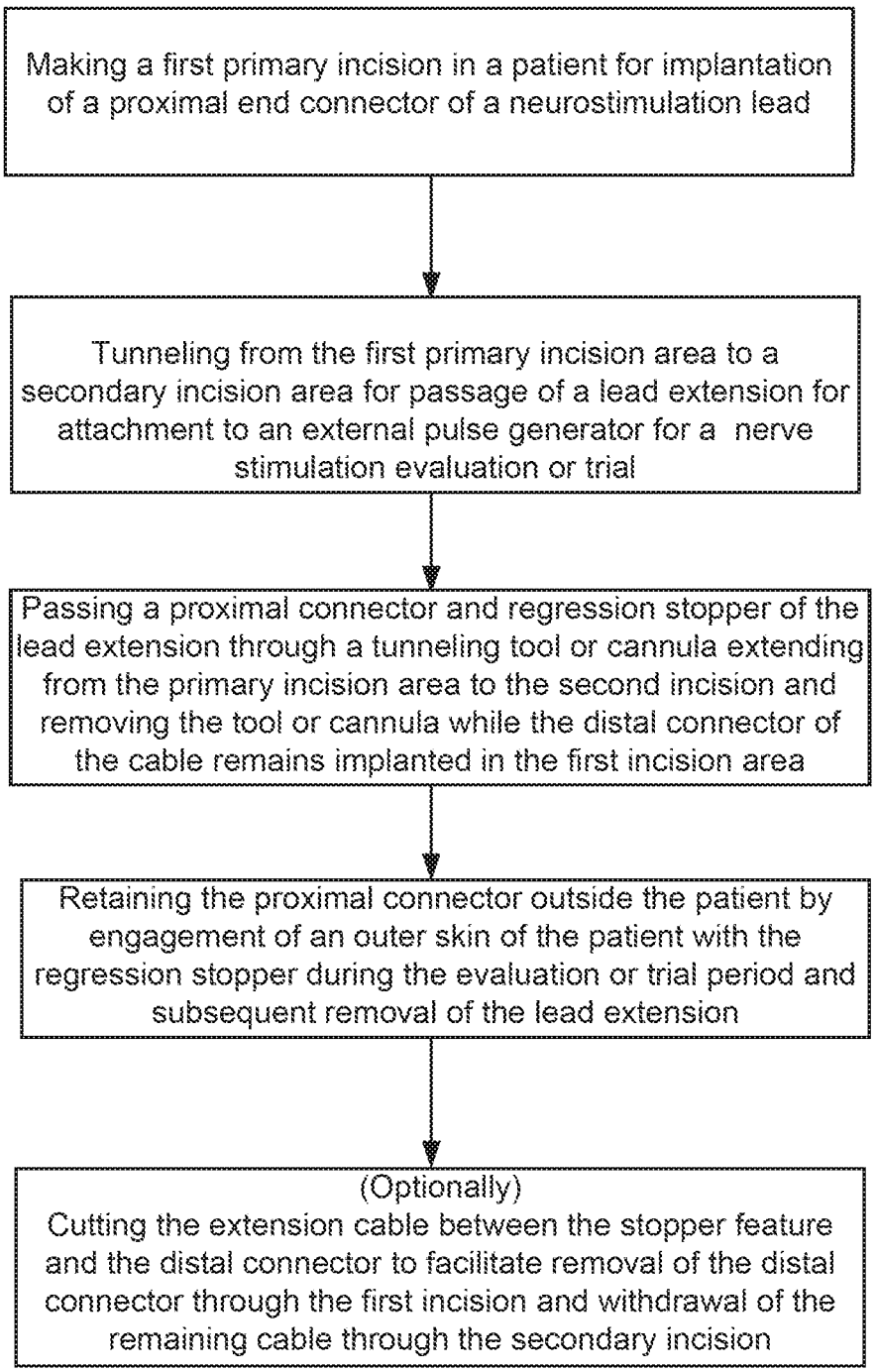
FIG. 17 illustrate a method of use of a neurostimulation lead extension cable for a neurostimulation trial period in accordance with some embodiments.

FIG. 17 depicts a method of utilizing a lead extension. Such methods can include: implanting a neurostimulation lead in a body of a patient such that a proximal end of the lead is disposed at a first incision area; tunneling from the first incision area to a second incision; connecting a distal connector of the lead extension at the first incision area and implanting the distal connector at the first incision area, the distal connector being electrically coupled with a proximal connector of the lead extension via an extension cable including a regression stopper; and passing a proximal connector and the regression stopper through a tool or cannula tunneled from the first incision and through the second incision outside the patient's body. The tool or cannula are then removed. Engaging, with the regression stopper, an outer skin of the patient or a pad or gauze disposed thereon inhibit regression of the lead into the patient during a trial period or during explant of the lead extension. This prevents infection of the second incision site and facilitates removal of the lead extension after the trial.

In regard to trial leads generally, for example a PNE lead, it is desirable for such leads to be configured to fit within a delivery needle or cannula, such as a 20 gauge needle with an ID of 0.025". Typically, such leads include at least one conductor and one distal electrode for monopolar stimulation. In some embodiments, trial leads can include multiple leads to allow for mono-polar stimulation at differing points during the trial, or to allow for bi-polar stimulation or sequential stimulation between differing electrodes. In some embodiments, trial leads include tissue retention features that minimize acute migration of the lead during the trial period.

FIG. 18-23C depict various other features of neurostimulation leads. It is appreciated that such features can pertain to any type of neurostimulation lead, for example the trials leads, such as a PNE lead, or to permanently implanted leads, as well as any type of neurostimulation application.

FIG. 18 depicts a coating of a neurostimulation lead 20 having barbs 75. Such barbs 75 can be configured unidirectionally to inhibit migration of the lead in one direction, or bi-laterally so as to inhibit lead migration in either direction. The barbs can be cut into the insulating coating of the conductor. Alternatively, the conductor could pass through a lead body that includes barbed retention features.

FIGS. 19A-19C illustrate a coiled conductor lead 76 defined by a multi-conductor ribbon 78. As shown in the cross-section of FIG. 19C, the multi-conductor ribbon 78 includes multiple conductors 77, each having an insulated coating and fixed in a line along the ribbon. The lead body is defined by the multi-conductor ribbon and can be entirely closed wound, open coiled, or have combinations of portions that are closed wound and open coiled. The distal portions of each conductor can be exposed so as to form a distal electrode, the differing conductors being exposed along differing locations along the lead so as to provide a multi-electrode lead.

In another aspect, a multi-electrode neurostimulation lead can be defined by a multiple conductors wound along a spiral or helical lead body. In some embodiments, such leads can includes a lead body defined by a helix of conductors attached on an outside of a lumen tubing. The helical twists along the length of the lead body provide textural surfaces that provide for improve tissue retention. It is appreciated that any of the other features described herein (e.g. barbs) can also be used in combination with these features. FIGS. 20A-20B illustrate cross-sectional view of two examples of such neurostimulation leads. FIG. 20A illustrates four conductors 78 wound about a central core or central lumen 79, the conductors being attached to an outer surface of the lumen tubing 79a. FIG. 20A illustrates eight insulated conductors 78 wound about a central lumen 79, the conductors being attached to an outer surface of the lumen tubing 79a. An additional outer coating 80' can be applied along the outside of the conductors.

In another aspect, anchoring features for use with implantable neurostimulation leads are provided. Such features can be applied to trial leads, such as PNE leads, so as to maintain a position of the lead and improve accuracy of the trial assessment as well as permanently implanted leads. In some embodiments, the neurostimulation lead includes a retractable anchor, a bioabsorbable anchor, and/or a bioabsorbable anchor with a radiopaque marker.

Figure 21A:
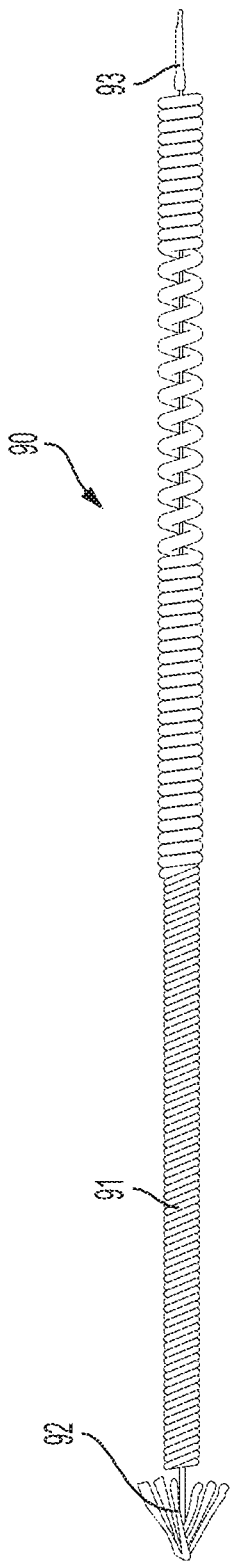
FIGS. 21A-21B illustrate a coiled neurostimulation lead having a retractable anchor feature, before and after retraction respectively, in accordance with some embodiments.
Figure 21B:
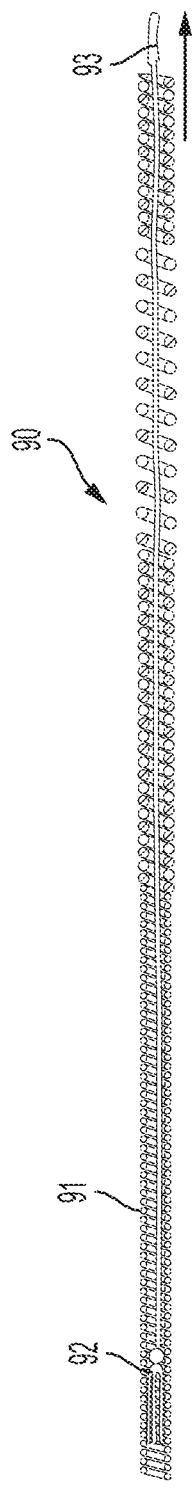

FIGS. 21A-21B show a neurostimulation lead 90 defined by a coiled conductor 91 that includes a distal anchor 92 that is retractable into a central lumen by retraction of an elongate member 93, such as pullwire or tether, coupled to the anchor. FIGS. 21A and 21B show the lead 90 before and after retraction of the anchor 92.

Figure 22:
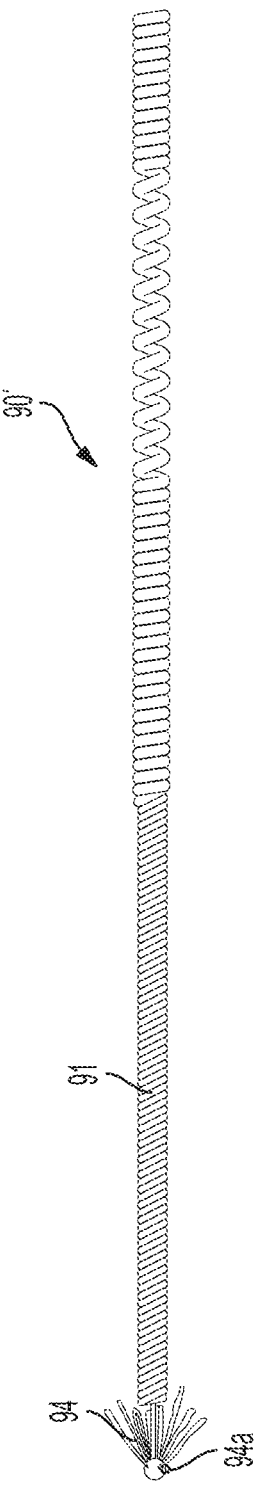
FIG. 22 illustrates a coiled neurostimulation lead having a bioabsorbable anchor feature in accordance with some embodiments.

FIG. 22 shows a neurostimulation lead 90' defined by a coiled conductor 91 and having a distal anchor 94 that is made of a bioabsorbable polymer which dissolves within the time period of the implant so as to allow for easy removal of the lead during explant. Optionally, the bioabsorbable lead contains a nonabsorbable radiopaque marker 94a, which is left behind to be used as a location marker for permanent implantation. The marker can be made of gold or platinum/iridium, or any suitable material.

In one aspect, the coiled lead includes an open pitch coil design or one or more portions having an open pitch coil design along portions of the lead that are implanted. The open coiled markers noted above in regard to the markers remain outside the body. By including such open coil portions along the implantable length, the gaps between coil and/or texture of the open coils provide more resistance to migration or regression of the lead. This feature can be utilized in any type of neurostimulation lead.

In another aspect, anchoring features can include a helical tined anchor attached to the lead. Such a helical tined anchor can be attached over an outside of the lead along the lead body, along the electrode or adjacent thereto. In some embodiments, the helical anchor can be attached by placement within an open pitch coiled region of the lead. In other embodiments, the helical tined anchor can be attached to a distal end of the lead and can also function as a lead stop for the stylet.

Figure 23A:
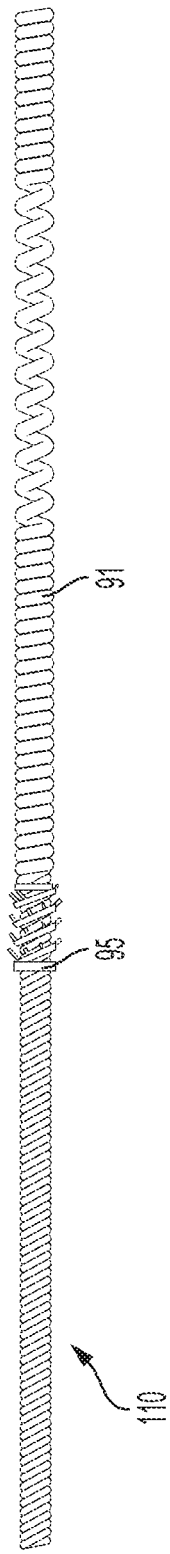
FIGS. 23A, 23B and 23C illustrate coiled neurostimulation leads having anchoring features that interface within coiled portions of the lead in accordance with some embodiments.
Figure 23B:
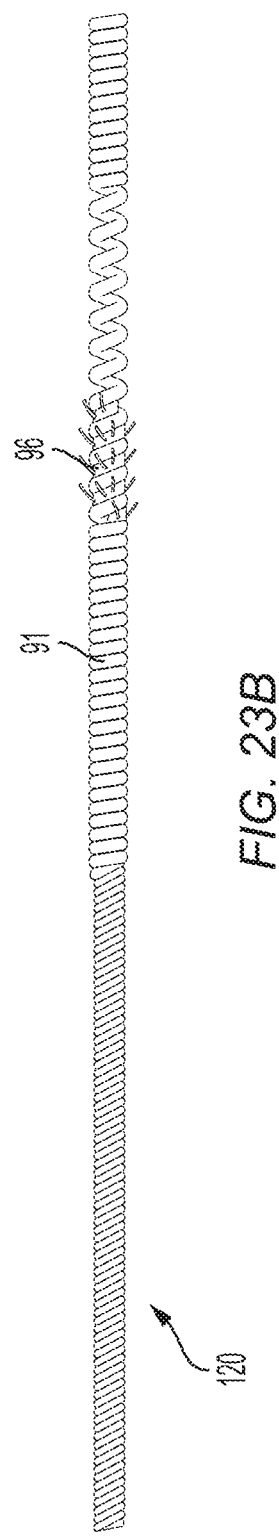
Figure 23C:
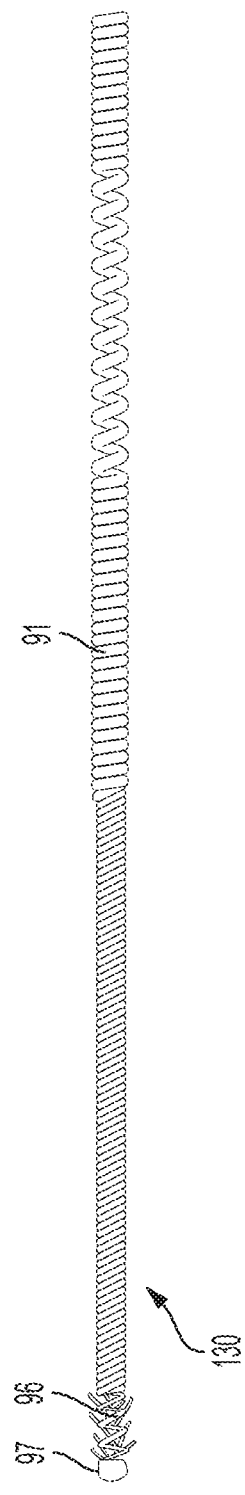

FIG. 23A shows a neurostimulation lead 110 defined by a coiled conductor 91 and having a helical tined anchor 95 attached on the outside of the lead body along the electrode portion. FIG. 23B shows a neurostimulation lead 120 having helical tined anchor 96 intertwined within an open pitched region of the lead body. FIG. 23C shows a neurostimulation lead 130 having a distal helical tined anchor 96 attached to a distal end of the lead and that further includes a distal atraumatic tip 97 that acts as an end stop for the stylet during implantation. In any such embodiments, the helical pitch of the helical tined anchor can be defined to match the pitch within the region of the lead body to which it is attached. The anchor can be formed of any suitable material (e.g. polymer, metal, etc.). In some embodiments, the helical anchor is formed of Nitinol tubing cut into a helical configuration. The protruding tines can be heat set into the expanded position. The Nitinol helical base can be heat set to a smaller inner diameter than the lead body to provide an interference fit, which can then be twisted to open and then loaded onto the lead body. Upon release, the helical base automatically tightens onto the lead body providing a secure attachment to the lead. While these features are described in regard to a single electrode coiled conductor lead, typically utilized as a trial lead, it is appreciated that any of these features could be utilized in a various other types of leads, such as multi-electrode leads or permanently implanted leads, or various other applications.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A neurostimulation lead comprising:
   at least one coiled conductor extending from a proximal portion of the neurostimulation lead to a distal electrode on a distal portion of the neurostimulation lead;
   a proximal contact connector electrically coupled with a proximal portion of the at least one coiled conductor and configured for electrically connecting the lead to a pulse generator or an intermediary cable,
   wherein the proximal contact connector includes a distal retention flange and a reduced profile coupling portion proximal of the distal retention flange,
   wherein one or more coils of the at least one coiled conductor are positioned along the coupling portion and fixedly attached thereto,
   wherein at least a portion of the one or more coils engage a proximal facing surface of the retention flange so as to resist tension within the coiled lead and maintain integrity of electrical connection between the coiled conductor and the proximal contact connector,
   wherein the retention flange includes a distal facing ramped surface extending at least partly about the circumference of the proximal contact connector to facilitate assembly of the coiled conductor with the proximal contact connector,
   wherein the retention flange includes an open notch portion having a reduced radius as compared to a remainder of the flange so as to allow the coiled conductor to be screwed onto the coupling portion past the flange.

2. The neurostimulation lead of claim 1, wherein the open notch portion is between 90 to 160 degrees about a circumference of the retention flange.

3. The neurostimulation lead of claim 1, wherein the ramped surface of the retention flange is ramped at an angle between 30 and 60 degrees.

4. The neurostimulation lead of claim 1, wherein the proximal facing retention surface of the retention flange extends substantially perpendicular to a longitudinal axis of the proximal contact connector.

5. The neurostimulation lead of claim 1, wherein the coiled conductor is fixedly attached and electrically coupled to the coupling portion of the proximal contact connector by soldering or laser welding.

6. The neurostimulation lead of claim 1, wherein the proximal contact connector includes a proximal portion that is elongate to facilitate connection of the lead to a pulse generator and includes a proximal opening to facilitate introduction of a stylet through an open lumen of the lead.

7. The neurostimulation lead of claim 1, further comprising:
   an outer insulator coating disposed on the at least one coiled conductor along at least an intermediate portion of the neurostimulation lead between the proximal portion and the distal electrode, wherein the distal electrode is defined by an exposed portion of the coiled conductor without the outer insulator coating.

8. The neurostimulation lead of claim 1, wherein the neurostimulation lead has substantially the same outer diameter along the at least one coiled conductor and the proximal contact connector to facilitate passage of the lead through a foramen needle.

9. The neurostimulation lead of claim 1, wherein a majority of the coiled conductor is closed wound at a first pitch.

10. The neurostimulation lead of claim 1, wherein the neurostimulation lead is configured for sacral nerve stimulation.

11. The neurostimulation lead of claim 10, wherein the neurostimulation lead is configured as a trial stimulation lead for percutaneous nerve evaluation.

12. The neurostimulation lead of claim 11, wherein a length or surface area of the distal electrode corresponds to a dimension of an electrode portion of an implantable neurostimulation lead to be placed after percutaneous nerve evaluation.

13. The neurostimulation lead of claim 1, further comprising:
one or more additional conductors extending from the proximal portion of the neurostimulation lead to one or more additional electrodes along the distal portion of the neurostimulation lead.

14. The neurostimulation lead of claim 13, wherein the one or more additional coiled conductors are electrically coupled and fixedly attached to the coupling portion of the proximal contact connector and one or more coils of each of the one or more additional coiled conductors are disposed proximal of the retention flange.

15. The neurostimulation lead of claim 13, wherein the coiled conductor and the one or more additional conductors are defined by a multi-ribbon conductor.

16. The neurostimulation lead of claim 13, wherein the coiled conductor and the one or more additional conductors are defined by multiple insulated conductors wound about a tube having a central lumen.

17. The neurostimulation lead of claim 1, wherein a coating of the coiled conductor comprises a textured surface configured to provide improved retention.

18. The neurostimulation lead of claim 1, wherein an outer coating of the coiled conductor includes a barbed surface having a plurality of barbs oriented to inhibit movement of the neurostimulation lead.

19. The neurostimulation lead of claim 1, further comprising:
a retractable anchoring feature at a distal end of the lead, the anchoring feature attached to an elongate member extending through the proximal contact connector such that retraction of the elongate member retracts the distal anchor into a central lumen of the coiled conductor.

20. The neurostimulation lead of claim 1, further comprising:
a bioabsorbable anchor disposed at a distal end of the lead or adjacent the distal electrode, the anchor being configured to absorb after expiration of the trial period to allow ready removal of the lead.

21. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange,
wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector, and
a helical tined anchor configured to attach to the coiled conductor.

22. The neurostimulation lead of claim 21, wherein the helical tined anchor is wound at a same pitch as a portion of the conductor to which the anchor is attached.

23. The neurostimulation lead of claim 21, wherein the helical tined anchor is formed of polymer.

24. The neurostimulation lead of claim 21, wherein the helical tined anchor is configured to attach to an outer surface of a closed wound portion of the lead along or adjacent the distal electrode.

25. The neurostimulation lead of claim 24, wherein the helical tined anchor is further configured to attach to a distal end of the lead and includes a distal atraumatic tip to provide an end stop for a stylet inserted within the coiled conductor.

26. The neurostimulation lead of claim 21, further comprising:
a helical tined anchor configured to attach to an interior portion of an open coil pitch portion of the coiled conductor such that the tines extend outward from the lead.

27. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes:
a reduced profile coupling portion along a distal portion thereof, along which the at least one coiled conductor is connected by a weld joint;
a distal retention feature of the proximal contact connector, wherein the distal retention feature comprises engagement of a plurality of coils of the at least one conductor along a surface of the proximal contact connector distal of the weld joint to reduce a load and stress concentration at the weld joint, thereby maintaining integrity of the weld joint,
wherein the distal retention feature is configured to withstand a minimal tensile force of at least 5 N.

28. The neurostimulation lead of claim 27, wherein the distal retention feature further comprises a distal end of the proximal contact connector that is sized to be fittingly received within an inner diameter of the plurality of coils of the at least one coiled conductor.

29. The neurostimulation lead of claim 27, wherein the distal retention feature further comprises a retention flange.

30. The neurostimulation lead of claim 27, wherein the weld joint is a laser weld.

31. The neurostimulation lead of claim 27, wherein the neurostimulation lead is configured as a trial stimulation lead for percutaneous nerve evaluation.

32. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange, wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector,
wherein the retention flange is configured to withstand a tensile force of at least 5 N.

33. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange,
wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector,
wherein the retention flange is configured to withstand a minimum tensile force of 10-12 N.

34. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange,
wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector,
wherein a majority of the coiled conductor is closed wound at a first pitch,
wherein coiled conductor includes one or more open coiled portions wound at a second pitch, wherein the one or more coiled portions are positioned at a distance from the distal electrode that corresponds to a length of one or more foramen needles.

35. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange,
wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector,
wherein the distal electrode has a surface area within a range of about 0.01 in$^2$ to 0.1 in$^2$.

36. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange,
wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector,
wherein the coiled conductor includes an open coil pitch along at least a portion of an implantable length of the lead so as to resist migration of the lead.

37. A neurostimulation lead comprising:
at least one coiled conductor extending from a proximal portion of the neurostimulation lead to a distal electrode on a distal portion of the neurostimulation lead;
a proximal contact connector electrically coupled with a proximal portion of the at least one coiled conductor and configured for electrically connecting the lead to a pulse generator or an intermediary cable,
wherein the proximal contact connector includes a distal retention flange and a reduced profile coupling portion proximal of the distal retention flange,
wherein one or more coils of the at least one coiled conductor are positioned along the coupling portion and fixedly attached thereto,
wherein at least a portion of the one or more coils engage a proximal facing surface of the retention flange so as to resist tension within the coiled lead and maintain integrity of electrical connection between the coiled conductor and the proximal contact connector; and
a bioabsorbable anchor disposed at a distal end of the lead or adjacent the distal electrode, the anchor being configured to absorb after expiration of the trial period to allow ready removal of the lead;
wherein the bioabsorbable anchor includes a radiopaque marker that remains within the body after the anchor absorbs to allow positioning of an electrode of a permanently implanted lead at the same location as the distal electrode of the lead.

* * * * *